US012740727B2

(12) United States Patent
Jang et al.

(10) Patent No.: US 12,740,727 B2
(45) Date of Patent: Sep. 22, 2026

(54) MEASURING NEUROCHEMICAL LEVELS WITH MULTIPLE CYCLIC SQUARE WAVE VOLTAMMETRY

(71) Applicants: Mayo Foundation for Medical Education and Research, Rochester, MN (US); INDUSTRY-UNIVERSITY COOPERATION FOUNDATION HANYANG UNIVERSITY, Seoul (KR)

(72) Inventors: Dong-Pyo Jang, Sungnam City (KR); Kendall H. Lee, Rochester, MN (US); Yoonbae Oh, Rochester, MN (US); Christopher J. Kimble, Pine Island, MN (US)

(73) Assignees: Mayo Foundation for Medical Education and Research, Rochester, MN (US); Industry-University Cooperation Foundation Hanyang University, Seoul (KR)

( * ) Notice: Subject to any disclaimer, the term of this patent is extended or adjusted under 35 U.S.C. 154(b) by 992 days.

(21) Appl. No.: 17/270,671

(22) PCT Filed: Aug. 20, 2019

(86) PCT No.: PCT/US2019/047219
§ 371 (c)(1),
(2) Date: Feb. 23, 2021

(87) PCT Pub. No.: WO2020/041277
PCT Pub. Date: Feb. 27, 2020

(65) Prior Publication Data

US 2021/0341412 A1 Nov. 4, 2021

Related U.S. Application Data

(60) Provisional application No. 62/722,059, filed on Aug. 23, 2018.

(51) Int. Cl.
*A61B 5/145* (2006.01)
*G01N 27/327* (2006.01)
(Continued)

(52) U.S. Cl.
CPC ..... *A61B 5/14546* (2013.01); *G01N 27/3277* (2013.01); *G01N 33/48707* (2013.01); *A61B 5/1473* (2013.01)

(58) Field of Classification Search
None
See application file for complete search history.

(56) References Cited

U.S. PATENT DOCUMENTS 3,914,623 A 10/1975 Clancy
8,803,569 B1 8/2014 Malladi et al.
(Continued)

FOREIGN PATENT DOCUMENTS

WO WO 2020/041277 2/2020

OTHER PUBLICATIONS

EP Extended Search Report in European Appln. No. 19852647.7, dated Feb. 8, 2022, 7 pages.
(Continued)

*Primary Examiner* — Aurelie H Tu
(74) *Attorney, Agent, or Firm* — Fish & Richardson P.C.

(57) ABSTRACT

Systems, methods, and devices for generating multiple cyclic square-waveforms and sloped-edge square wave-forms. Aspects of the techniques disclosed herein include applying the generated waveforms to an electrode used in voltammetry, e.g., to measure a level of a neurochemical in neural tissue. An electrode can be located in a solution, and an electrical stimulus applied to the solution through the electrode using a multiple cyclic square waveform. An electrical current response to the stimulus is measured, and
(Continued)

a level of an analyte (e.g., dopamine or other neurochemical(s)) determined based on the electrical current response.

8 Claims, 29 Drawing Sheets

(51) Int. Cl.
*G01N 33/487* (2006.01)
*A61B 5/1473* (2006.01)

(56) References Cited

U.S. PATENT DOCUMENTS

| | | | | |
|---|---|---|---|---|
| 9,347,900 | B2 | 5/2016 | Korlach et al. | |
| 2004/0086892 | A1 | 5/2004 | Crothers et al. | |
| 2008/0302673 | A1* | 12/2008 | Scheffler | G01N 33/0006 204/412 |
| 2011/0084739 | A1 | 4/2011 | Yu et al. | |
| 2011/0241694 | A1 | 10/2011 | Burke et al. | |
| 2014/0330096 | A1* | 11/2014 | Brunswick | A61B 5/0531 600/383 |
| 2016/0007900 | A1 | 1/2016 | Veale et al. | |
| 2020/0178864 | A1 | 6/2020 | Cui et al. | |

OTHER PUBLICATIONS

Jadreško et al., "Cyclic multipulse voltammetric techniques. Part I: Kinetics of electrode processes," J. Electroanal. Chemistry, Oct. 15, 2013, 707:20-30.
Yuen et al., "Cocaine-Induced Changes in Tonic Dopamine Concentrations Measured Using Multiple-Cyclic Square Wave Voltammetry in vivo," Front. Pharmacology, Jul. 6, 2021, 12:705254, 10 pages.
Abdalla et al., "In Vivo Ambient Serotonin Measurements at Carbon-Fiber Microelectrodes," Anal. Chemistry, Aug. 10, 2017, 89(18):9703-9711.
Atcherley et al., "Fast-Scan Controlled-Adsorption Voltammetry for the Quantification of Absolute Concentrations and Adsorption Dynamics," Langmuir, Nov. 18, 2013, 29(48):14885-14892.
Atcherley et al., "The coaction of tonic and phasic dopamine dynamics," Chem. Communications, Feb. 11, 2015, 51(12):2235-2238.
Balleine et al., "The Role of the Dorsal Striatum in Reward and Decision-Making," J. Neuroscience, Aug. 1, 2007, 27(31):8161-8165.
Barath et al., "Hypoxia-Associated Changes in Striatal Tonic Dopamine Release: Real-Time in vivo Measurements With a Novel Voltammetry Technique," Front. Neuroscience, Aug. 18, 2020, 14:869, 8 pages.
Bath et al., "Subsecond Adsorption and Desorption of Dopamine at Carbon-Fiber Microelectrodes," Anal. Chemistry, Nov. 17, 2000, 72(24):5994-6002.
Blaha, "Evaluation of Stearate-Graphite Paste Electrodes for Chronic Measurement of Extracellular Dopamine Concentrations in the Mammalian Brain," Pharmacol. Biochem. Behavior, Nov. 1996, 55(3):351-364.
Burrell et al., "A Novel Electrochemical Approach for Prolonged Measurement of Absolute Levels of Extracellular Dopamine in Brain Slices," ACS Chem. Neuroscience, Aug. 31, 2015, 6(11):1802-1812.
Cahill et al., "Microelectrodes for the Measurement of Catecholamines in Biological Systems," Anal. Chemistry, Sep. 15, 1996, 68(18):3180-3186.
Carboni et al., "Blockade of the Noradrenaline Carrier Increases Extracellular Dopamine Concentrations in the Prefrontal Cortex: Evidence that Dopamine Is Taken up In Vivo by Noradrenergic Terminals," J. Neurochemistry, Sep. 1990, 55(3):1067-1070.
Caron et al., "Dopaminergic receptors in the anterior pituitary gland: Correlation of [3H]dihydroergocryptine binding with the dopaminergic control of prolactin release," J. Biol. Chemistry, Apr. 1978, 253(7):2244-2253.
Chang et al., "Development of the Mayo Investigational Neuromodulation Control System: toward a closed-loop electrochemical feedback system for deep brain stimulation," J. Neurosurgery, Oct. 11, 2013, 119(6):1556-1565.
Chang et al., "Wireless fast-scan cyclic voltammetry to monitor adenosine in patients with essential tremor during deep brain stimulation," Mayo Clin, Proceedings, Jul. 16, 2012, 87(8):760-765.
Collins et al., "Nucleus Accumbens Acetylcholine Receptors Modulate Dopamine and Motivation," Neuropsychopharmacology, May 31, 2016, 41(12):2830-2838.
Davis et al., "Dopamine in Schizophrenia: A Review and Reconceptualization," Am. J. Psychiatry, Nov. 1991, 148(11):1474-1486.
Dengler et al., "Microfabricated microelectrode sensor for measuring background and slowly changing dopamine concentrations," J. Electroanal. Chemistry, Feb. 4, 2013, 693:28-33.
DeWaele et al., "A baseline drift detrending technique for fast scan cyclic voltammetry," Analyst, Nov. 6, 2017, 142(22):4317-4321.
Ding et al., "Development of Glass-sealed Gold Nanoelectrodes for in vivo Detection of Dopamine in Rat Brain," Electroanalysis, Jun. 2018, 30(6):1041-1046.
Espin et al., "Integral methods for automatic quantification of fast-scan-cyclic-voltammetry detected neurotransmitters," bioRxiv, Apr. 27, 2020, 13 pages.
Ewing et al., "Simultaneous Electrochemical and Unit Recording Measurements: Characterization of the Effects of D-Amphetamine and Ascorbic Acid on Neostriatal Neurons," Brain Research, Feb. 14, 1983, 261(1):101-108.
Fisher, "Statistical Methods for Research Workers," in Breakthroughs in Statistics, 1992, 66-70.
Floresco et al., "Afferent modulation of dopamine neuron firing differentially regulates tonic and phasic dopamine transmission," Nat. Neuroscience, Aug. 3, 2003, 6(9):968-973.
Gonon et al., "Voltammetry in the striatum of chronic freely moving rats: detection of catechols and ascorbic acid," Brain Research, Oct. 26, 1981, 223(1):69-80.
Goto et al., "The Yin and Yang of dopamine release: a new perspective," Neuropharmacology, Jul. 19, 2007, 53(5):583-587.
Grace et al., "The control of firing pattern in nigral dopamine neurons: burst firing," J. Neuroscience, Nov. 1984, 4(11):2877-2890.
Grace, "Dysregulation of the dopamine system in the pathophysiology of schizophrenia and depression," Nat. Rev. Neuroscience, Jun. 3, 2016, 17(8):524-532.
Grace, "Phasic versus tonic dopamine release and the modulation of dopamine system responsivity: a hypothesis for the etiology of schizophrenia," Neuroscience, 1991, 41(1):1-24.
Grace, "The tonic/phasic model of dopamine system regulation and its implication for understanding alcohol and psychostimulant craving," Addiction, 2000, 95(8S2):S119-S128.
Gu et al., "In Vivo Monitoring of Dopamine by Microdialysis with 1 min Temporal Resolution Using Online Capillary Liquid Chromatography with Electrochemical Detection," Anal, Chemistry, May 13, 2015, 87(12):6088-6094.
Heien et al., "Overoxidation of carbon-fiber microelectrodes enhances dopamine adsorption and increases sensitivity," Analyst, Nov. 11, 2003, 128(12):1413-1419.
Helen et al., "Phasic Dopamine Signaling During Behavior, Reward, and Disease States," CNS Neurol. Disord. Drug Targets, Feb. 2006, 5(1):99-108.
Heien et al., "Real-time measurement of dopamine fluctuations after cocaine in the brain of behaving rats," Proc. Nat. Acad. Sci. USA, Jul. 19, 2005, 102(29):10023-10028.
Heien et al., "Resolving Neurotransmitters Detected by Fast-Scan Cyclic Voltammetry," Anal. Chemistry, Sep. 3, 2004, 76(19):5697-5704.
Helfrick Jr et al., "Cyclic Square Wave Voltammetry of Single and Consecutive Reversible Electron Transfer Reactions," Anal, Chemistry, Oct. 2, 2009, 81(21):9041-9047.
Hornykiewicz, "The Discovery of Dopamine Deficiency in the Parkinsonian Brain," J. Neural Transm. Supplementa, 2006, 70:9-15.

(56) References Cited

OTHER PUBLICATIONS

Howell et al., "Background subtraction for rapid scan voltammetry," J. Electroanal. Chem. Interfacial Electrochemistry, Sep. 10, 1986, 209(1):77-90.
Huffman et al., "Carbon-fiber microelectrodes for in vivo applications," Analyst, Jan. 2009, 134(1):18-24.
Hyman et al., "Addiction and the brain: The neurobiology of compulsion and its persistence," Nat. Rev. Neuroscience, Oct. 1, 2001, 2(10):695-703.
Jang et al., "Paired pulse voltammetry for differentiating complex analytes," Analyst, Feb. 2, 2012, 137(6):1428-1435.
Jay, "Dopamine: a potential substrate for synaptic plasticity and memory mechanisms," Prog. Neurobiology, Apr. 2003, 69(6):375-390.
Johnson et al., "Failure of Standard Training Sets in the Analysis of Fast-Scan Cyclic Voltammetry Data," ACS Chem. Neuroscience, Jan. 12, 2016, 7(3):349-359.
Johnson et al., "Measurement of Basal Neurotransmitter Levels Using Convolution-Based Nonfaradaic Current Removal," Anal. Chemistry, Jun. 7, 2018, 90(12):7181-7189.
Justice Jr. "Quantitative microdialysis of neurotransmitters," J. Neurosci. Methods, Jul. 1993, 48(3):263-276.
Keithley et al., "Higher Sensitivity Dopamine Measurements with Faster-Scan Cyclic Voltammetry," Anal. Chemistry, Apr. 7, 2011, 83(9):3563-3571.
Kim et al., "Automatic and reliable quantification of tonic dopamine concentrations in vivo using a novel probabilistic inference method," ACS Omega, Mar. 3, 2021, 6(10):6607-6613.
Kim et al., "Multi-waveform fast-scan cyclic voltammetry mapping of adsorption/desorption kinetics of biogenic amines and their metabolites," Anal. Methods, May 23, 2018, 10(24):2834-2843.
Kishida et al., "Subsecond dopamine fluctuations in human striatum encode superposed error signals about actual and counterfactual reward," Proc. Natl. Acad. Sci. USA, Jan. 5, 2016, 113(1):200-205.
Koo et al., "Role of dopamine in the pathophysiology and treatment of obsessive-compulsive disorder," Expert Rev. Neurotherapy, Feb. 2010, 10(2):275-290.
LeDoux, "Rethinking the emotional brain," Neuron, Feb. 23, 2012, 73(4):653-676.
Lee et al., "Dopamine efflux in the rat striatum evoked by electrical stimulation of the subthalamic nucleus: Potential mechanism of action in Parkinson's disease," Eur. J. Neuroscience, Feb. 2006, 23(4):1005-1014.
Lee et al., "WINCS Harmoni: Closed-loop dynamic neurochemical control of therapeutic interventions," Sci. Reports, Apr. 28, 2017, 7:46675, 14 pages.
Nelder et al., "Generalized Linear Models," J. R. Statist. Soc. Series A, 1972, 135(3):370-384.
Nirenberg et al., "The Dopamine Transporter Is Localized to Dendritic and Axonal Plasma Membranes of Nigrostriatal Dopaminergic Neurons," J. Neuroscience, Jan. 15, 1996, 16(2):436-447.
Oh et al., "Monitoring In Vivo Changes in Tonic Extracellular Dopamine Level by Charge-Balancing Multiple Waveform Fast-Scan Cyclic Voltammetry," Anal, Chemistry, Oct. 24, 2016, 88(22):10962-10970.
Oh et al., "Optimization of Paired Pulse Voltammetry Using Sawhorse Waveform," Int. J. Electrochem. Science, Nov. 4, 2015, 10(12):10061-10073.
Oh et al., "Tracking tonic dopamine levels in vivo using multiple cyclic square wave voltammetry," Biosens. Bioelectronics, Dec. 15, 2018, 121:174-182.
Osteryoung et al., "Square wave voltammetry," Anal. Chemistry, Jan. 1, 1985, 57(1):101-110.
Osteryoung, "Pulse voltammetry," J. Chem. Education, Apr. 1, 1983, 60(4):296-298.
Park et al., "Fast Cyclic Square-Wave Voltammetry to Enhance Neurotransmitter Selectivity and Sensitivity," Anal. Chemistry, Oct. 25, 2018, 90(22):13348-13355.
PCT International Preliminary Report on Patentability in International Appln. No. PCT/US2019/047219, dated Feb. 23, 2021, 6 pages.
PCT International Search Report and Written Opinion in International Appln. No. PCT/US2019/047219, dated Dec. 16, 2019, 9 pages.
PCT Invitation to Pay Additional Fees in International Appln. No. PCT/US2019/047219, dated Oct. 9, 2019, 2 pages.
Price et al., "Clinical applications of neurochemical and electrophysiological measurements for closed- loop neurostimulation," Neurosurg. Focus, Jul. 2020, 49(1):E6, 8 pages.
Radke et al., "Contributions of nucleus accumbens dopamine to cognitive flexibility," Eur. J. Neuroscience, Oct. 10, 2018, 50(3):2023-2035.
Robinson et al., "Detecting Subsecond Dopamine Release with Fast-Scan Cyclic Voltammetry in Vivo," Clin. Chemistry, Oct. 2003, 49(10):1763-1773.
Salamone, "Complex motor and sensorimotor functions of striatal and accumbens dopamine: involvement in instrumental behavior processes," Psychopharmacology, 1992, 107(2-3):160-174.
Schultz, "Multiple Dopamine Functions at Different Time Courses," Annu. Rev. Neuroscience, Mar. 12, 2007, 30:259-288.
Sesack et al., "Dopamine Axon Varicosities in the Prelimbic Division of the Rat Prefrontal Cortex Exhibit Sparse Immunoreactivity for the Dopamine Transporter," J. Neuroscience, Apr. 1, 1998, 18(7):2697-2708.
Shin et al., "Fornix Stimulation Induces Metabolic Activity and Dopaminergic Response in the Nucleus Accumbens," Front. Neuroscience, Oct. 24, 2019, 13:1109.
Shin et al., "Sensitive and Selective Measurement of Serotonin in Vivo Using Fast Cyclic Square-Wave Voltammetry," Anal. Chemistry, Dec. 16, 2019, 92(1):774-781.
Silverstone, "Dopamine in manic depressive illness: A pharmacological synthesis," J. Affect. Disorders, May-Jun. 1985, 8(3):225-231.
Slaney et al., "Chemical Gradients within Brain Extracellular Space Measured using Low Flow Push-Pull Perfusion Sampling in Vivo," ACS Chem. Neuroscience, Nov. 12, 2012, 4(2):321-329.
Stamford et al., "Simultaneous "real-time" electrochemical and electrophysiological recording in brain slices with a single carbon-fibre microelectrode," J. Neurosci. Methods, Dec. 1993, 50(3):279-290.
Stenken, "Methods and issues in microdialysis calibration," Anal. Chim. Acta, Jan. 18, 1999, 379(3):337-358.
Takahashi et al., "Measurement of Intracellular Calcium," Physiol. Reviews, Oct. 1999, 79(4):1089-1125.
Takmakov et al., "Carbon Microelectrodes with a Renewable Surface," Anal. Chemistry, Feb. 10, 2010, 82(5):2020-2028.
Taylor et al., "Direct in Vivo Electrochemical Detection of Resting Dopamine Using Poly(3,4-ethylenedioxythiophene)/Carbon Nanotube Functionalized Microelectrodes," Anal. Chemistry, Sep. 12, 2019, 91(20):12917-12927.
Venton et al., "Fundamentals of Fast-Scan Cyclic Voltammetry for Dopamine Detection," Analyst, Dec. 26, 2019, 145:1158-1168.
Volkow et al., "Dopamine in drug abuse and addiction: results of imaging studies and treatment implications," Arch. Neurology, Nov. 2007, 64(11):1575-1579.
Vreeland et al., "Biocompatible PEDOT:Nation Composite Electrode Coatings for Selective Detection of Neurotransmitters in Vivo," Anal. Chemistry, Feb. 18, 2015, 87(5):2600-2607.

* cited by examiner

[nA]
100
80
60
40
20
0
-20
-40
-60
-80
-100
Esw [V]
-0.4
+0.4
-0.2
0.9
-0.2
Staircase potential [V]

Esw [V]
-0.4
+0.4
1
0
-0.2
0.9
-0.2
Staircase potential [V]

Charge [pC]
0nM
50nM
100nM
200nM
500nM
1000nM
Time [min]

Charge [pC]
$R^2$=0.99
DA [nM]

| Method | Target location | Quantified tonic dopamine level | Refs |
|---|---|---|---|
| Amperometric monitoring with glass-sealed gold nanoelectrode | nucleus accumbens | 41 ± 13 nM | 7 |
| Fast-scan controlled-adsorption voltammetry | nucleus accumbens | 90 ± 9 nM | 8 |
| Microdialysis using online capillary liquid chromatography | striatum | 10.7 ± 1.5 nM | 9 |
| Reverse microdialysis with stearate-graphite paste electrodes | striatum | 86 ± 6 nM | 10 |
| Multiple cyclic square wave voltammetry | striatum | 120 ± 18 nM | This work |

FIG. 15

MEASURING NEUROCHEMICAL LEVELS WITH MULTIPLE CYCLIC SQUARE WAVE VOLTAMMETRY

CROSS-REFERENCE TO RELATED APPLICATIONS

This application is a National Stage application under 35 U.S.C. § 371 of International Application No. PCT/US2019/047219, having an International Filing Date of Aug. 20, 2019, which claims priority to U.S. Application Ser. No. 62/722,059, filed on Aug. 23, 2018. The disclosure of the prior application is considered part of the disclosure of this application, and is incorporated in its entirety into this application.

STATEMENT OF FEDERALLY SPONSORED RESEARCH

This invention was made with government support under NS090455 awarded by National Institutes of Health. The government has certain rights in the invention.

BACKGROUND

Fast-scan cyclic voltammetry (FSCV) has served as a reliable analytical technique for monitoring dopamine release in near real-time in vivo. However, contemporary FSCV techniques have been limited to measuring only rapid (e.g., on the order of seconds) (also referred to as 'phasic') changes in dopamine release evoked by either electrical stimulation or elicited by presentation of behaviorally salient stimuli, and not slower changes in the tonic extracellular levels of dopamine ('basal concentrations'). This is because FSCV is inherently a differential method that typically involves subtraction of prestimulation tonic levels of dopamine to measure phasic changes relative to a zeroed baseline.

Dopamine has a variety of roles in the brain, and is involved in learning and memory, motivation and emotional behaviors, and action-selection. Dysfunction in dopamine signaling is thus implicated in several neurologic and psychiatric diseases, including Parkinson's disease, drug addiction, depression, and schizophrenia. Dopamine neurons exhibit two distinct patterns of spike firing: tonic activity and phasic burst activity. Phasic activity causes a transient and robust release of dopamine that serves as a learning signal for neural plasticity. Tonic activity refers to spontaneous and continuous dopamine release driven by pacemaker-like firing of dopamine neurons, providing a tonic extracellular level of dopamine (i.e. basal concentration) in the striatum required to modulate behavioral flexibility. In addition, tonic dopamine concentrations are known to be modulated by the escape of dopamine from the extrasynaptic space, inhibition by GABAergic interneurons, receptor occupancy, dopamine transporter function, and synaptic plasticity.

SUMMARY

This specification discloses systems, methods, devices, and other techniques involving application of multiple cyclic square wave voltammetry (M-CSWV) for analytical quantification of analytes in a solution. In some implementations, the techniques apply M-CSWV to determine neurochemical (e.g., dopamine) concentrations in vivo with relatively high temporal resolution (e.g., 10 seconds). Through the disclosed M-CSWV techniques, analysis of sensed electrochemical information can be enhanced by generating two dimensional voltammograms which enable high sensitivity and selectivity against ascorbic acid, and 3,4-dihydroxyphenylacetic acid (DOPAC), including changes in pH.

M-CSWV can be applied in conjunction with a delayed holding potential period to control dopamine adsorption to the carbon fiber microelectrode (CFM) surface. Unlike conventional analysis of square wave voltammetric data, background currents recorded at all waveform points can be sampled and used to detect and quantify tonic dopamine concentrations. Dynamic background subtraction and capacitive background current simulation can be used to eliminate large capacitive background current, allowing tonic dopamine concentrations to be measured. Quantification of tonic dopamine concentrations (and quantification of tonic or basal levels of neurochemicals generally) is useful for a number of purposes. For example, in some implementations, a level (e.g., magnitude) or other characteristic of stimulation applied to neural tissue can be set as a function of the basal concentration of one or more neurochemicals as measured through M-CSWV. A closed-loop feedback system can be arranged in which a first carbon fiber microelectrode performs M-CSWV on or within a region of a brain (neural tissue) wile a second electrode is employed for neural stimulation. The stimulus applied by the second (stimulating) electrode can be periodically or continuously adjusted based one the results of measurements from M-CSWV (e.g., based on basal neurochemical concentrations).

The cyclic square waveform (CSW) can include a large-amplitude square wave modulation on top of a symmetric staircase waveform. Due to properties of this waveform, the voltammetric outcome of M-CSWV can provide a wealth of electrochemical information beyond that provided by conventional FSCV. Specially, multiple redox reactions of dopamine can occur within a scan that enables the technique to generate a two-dimensional voltammogram. Parameters of M-CSWV can be optimized in vitro to detect dopamine (e.g., at ten-second intervals).

In some aspects, a waveform generator configured is configured to arbitrarily vary the slope ($\Delta V/\Delta t$) of edges of the multiple cyclic square wave employed in M-CSWV. The effect of modulating the slopes of the waveform edges can be to reduce background currents that obscure Faradaic current measurements upon which the M-CSWV technique depends. By reducing background currents, these techniques can make it possible to increase the electrode surface area, improve signal-to-noise ratio, increase sensitivity, reduce voltage and power requirements of the signal-generating electronic circuitry, or achieve a combination of these advantages. In some implementations, the waveform generator is part of a voltammetric system configured to generate M-CSWV waveforms and record electrophysiological signals in tandem with voltammetry and synchronized neurostimulation.

Some implementations of the subject matter described herein include a method for measuring a level of an analyte in a solution. The method can include locating an electrode in the solution, applying an electrical stimulus to the solution, the electrical stimulus comprising a multiple cyclic square waveform (M-CSW), measuring an electrical current response to the electrical stimulus using the electrode that is located in the solution, measuring an electrical current response to the electrical stimulus using the electrode that is located in the solution, and determining the level of the analyte in the solution based on the electrical current response to the electrical stimulus.

These and other implementations can further include one or more of the following features.

The analyte can be dopamine or other neurochemical.

The solution can be a fluid in a brain of a mammal.

The electrode can be a carbon fiber microelectrode.

Determining the level of the analyte can include determining a tonic level of dopamine in the solution.

The M-CSW signal can include a square wave oscillation superimposed on a staircase waveform, wherein the staircase waveform has a rising phase and a falling phase.

The M-CSW includes sloped rising and falling edges.

The method can further include adjusting a slope of rising or falling edges of the M-CSW by adjusting a DC input voltage to a waveform generation circuit.

Some implementations of the subject matter described herein include generating a multiple cyclic square waveform (M-CSW), including controlling a slope of rising or falling edges of the M-CSW using an integrator circuit; and applying an electrical signal with an electrode, wherein the electrical signal is shaped according to the M-CSW.

Some implementations of the subject matter described herein include a method for generating a sloped-edge square waveform. The waveform can include a plurality of periods, and for each period the method can include generating the waveform for that period by: producing a rising edge of the waveform by (i) applying a first DC voltage as a first input to an integrator circuit for a first time interval and (ii) maintaining a capacitor in a de-clamped position for the first time interval; producing a high segment of the waveform to follow the rising edge by (i) switching the first input to the integrator circuit from the first DC voltage to a baseline DC voltage for a second time interval following the first time interval and (ii) maintaining the capacitor in the de-clamped position for the second time interval, wherein the high segment of the waveform maintains a high DC voltage for the second time interval, wherein the baseline DC voltage is less than the first DC voltage; producing a falling edge of the waveform to follow the high segment of the waveform by (i) switching the first input to the integrator circuit from the baseline DC voltage to a second DC voltage for a third time interval following the second time interval and (ii) maintaining the capacitor in the de-clamped position for the third time interval, wherein the second DC voltage is less than the first DC voltage and is less than the baseline DC voltage; and producing a low segment of the waveform to follow the falling edge of the waveform by (i) switching the first input to the integrator circuit from the second DC voltage to the baseline DC voltage for a fourth time interval and (ii) setting the capacitor in a clamped position for the fourth time interval.

These and other implementations can further include one or more of the following features.

The baseline DC voltage can be substantially zero Volts.

The first DC voltage can be a positive voltage of a first magnitude, and the second DC voltage can be a negative voltage of the first magnitude.

Setting the capacitor in the clamped position for the fourth time interval comprises using a switch to re-couple a first terminal of the capacitor from a first circuit node to a second circuit node.

Using a digital-to-analog converter to switch the first input from the first DC voltage to the baseline DC voltage.

The sloped-edge square waveform can be a multiple cyclic square waveform (M-CSW) with sloped edges. Generating the M-CSW with sloped edges can further include: (i) generating a cyclic staircase waveform and (ii) summing the sloped-edge square waveform with the cyclic staircase waveform.

The cyclic staircase waveform can include a plurality of cycles, each cycle having a first set of ascending steps and a second set of descending steps, wherein each step in the cycle corresponds to a respective DC voltage and has a duration equal to a single period of the sloped-edge square waveform.

In the de-clamped position, the capacitor can be connected directly to a non-inverting input of an operational amplifier of a ramp generation circuit.

DESCRIPTION OF DRAWINGS

FIG. 1A depicts a cyclic square waveform (CSW). FIG. 1B depicts an M-CSWV waveform. FIG. 1C depicts representative background currents measured by M-CSWV.

FIG. 2A: The background current difference between 2nd and last CSWV. FIG. 2B: Simulated background current difference between 2nd and last CSWV. FIG. 2C: Capacitive current removal by subtracting simulated CSWV from raw data. FIG. 2D: CSWV response for 1 μM of dopamine at different staircase potentials. FIG. 2E: Pseudo color plot of dopamine response to M-CSWV.

FIG. 3A: Dopamine 1 μM response to a number of CSW pulses. Dopamine responses from 1st to 4th waveform showed significant differences from the last voltammogram (Black bar, n=5 electrodes, $p<0.0001$, one-way ANOVA test with Dunnett's multiple comparisons). FIG. 3B: ESW effects on the dopamine response difference between 2nd and 5th M-CSWV. Dopamine responses are normalized. 0.4V $E_{SW}$ was significantly higher than others (n=3 electrodes, $p<0.0001$, one-way ANOVA test with Tukey's multiple comparisons). FIG. 3C: EHolding effects on the dopamine response difference between 2nd and 5th M-CSWV. Holding potentials from 0V to −0.4V showed no significant difference (n=5 electrodes, one-way ANOVA test).

FIG. 4A: Pseudo color plot of 1 μM dopamine response to M-CSWV. FIG. 4B: Dopamine kernel extracted from (A). Thresholding the pseudo color plot by 60% of the maximum amplitude set the top 40 percentiles (red, dopamine-featured area) to one and remaining (green) to zero. FIG. 4C: Steady-state current response obtained for the oxidation of dopamine at forward sweep upon the injection of multiple concentrations. FIG. 4D: A calibration plot obtained by M-CSWV correlates with dopamine concentrations (n=4 electrodes, R2=0.99, quadratic regression).

FIG. 5A: Peak oxidation currents of background-subtracted M-CSWV to DOPAC 20 μM. DOPAC responses from 2nd to 5th CSWV showed no significant differences (n=5, one-way ANOVA test, upper panel). Pseudo color plot of 2004 DOPAC response to M-CSWV. DOPAC can be offset by subtracting 2nd and 5th CSWV (lower panel). FIG. 5B: Peak oxidation currents of background-subtracted M-CSWV to AA 200 μM. AA responses from 2nd to 5th CSWV showed no significant differences (n=5, one-way ANOVA test, upper panel). Pseudo color plot of 2000 μM AA (lower panel). FIG. 5C:

Peak oxidation currents of background-subtracted M-CSWV to pH changes. pH responses from 1st to 5th CSWV showed no significant differences (n=5, one-way ANOVA test, upper panel). Pseudo color plot of pH changes (lower panel).

FIGS. 6A-6D illustrate pharmacological effects on tonic dopamine concentrations. The tonic dopamine concentrations in response to (A) no treatment controls (n=7 rats), (B) saline controls (n=5 rats), (C) nomifensine (n=5 rats, 20 mg kg-1, i.p.), and (D) pargyline (n=5 rats, 75 mg kg-1, i.p.). Bold line represents mean concentrations over time, and thin black lines represent the SEM. Bars above at the lower plots indicate significant differences compared to pre-drug injection (n=5 rats, each group, 2-way ANOVA, $p<0.0001$, Dunnett's multiple comparisons test).

Figure 7:
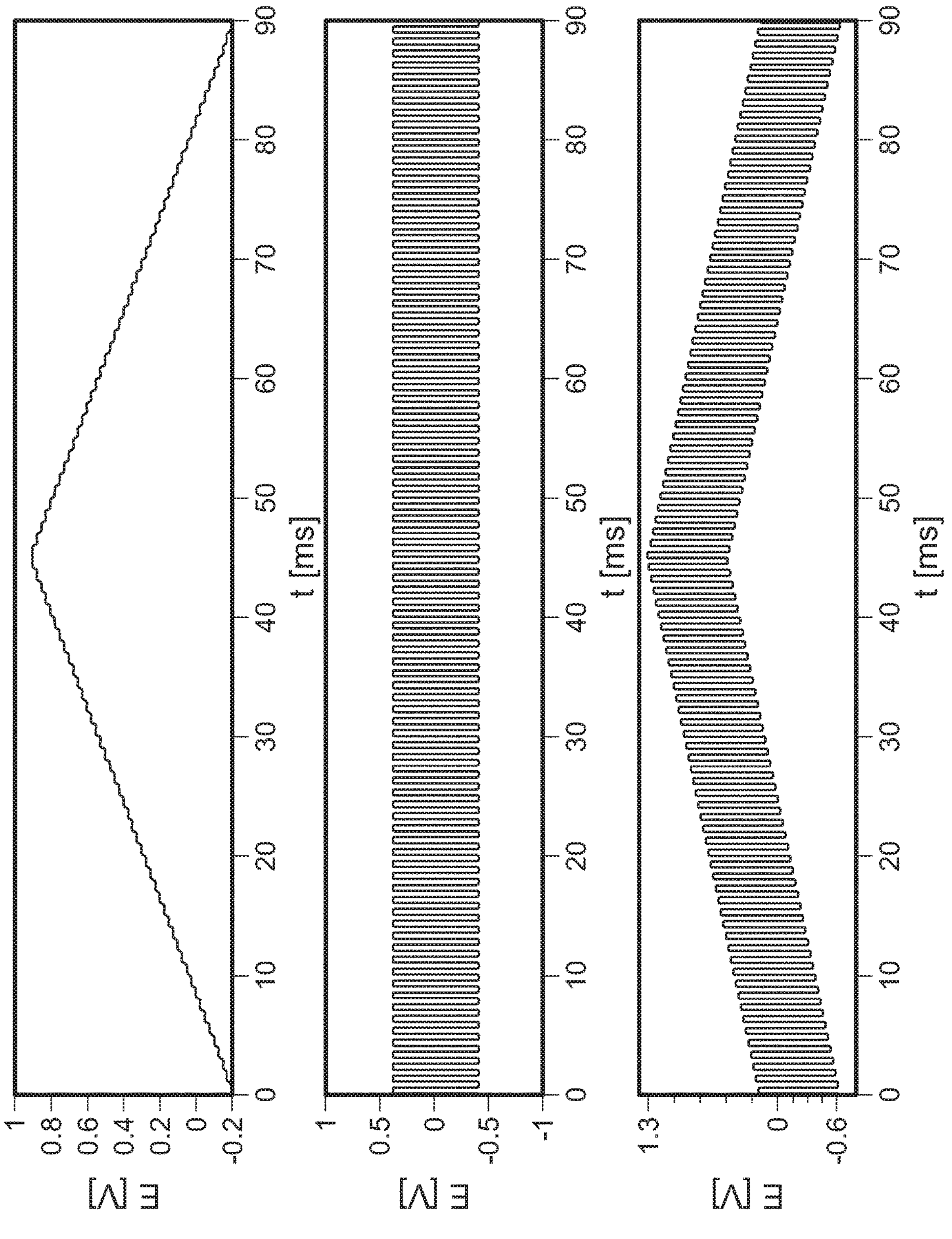

FIG. 7 depicts an example cyclic square waveform used throughout the example study.

Figures 8A, 8B, 8C:
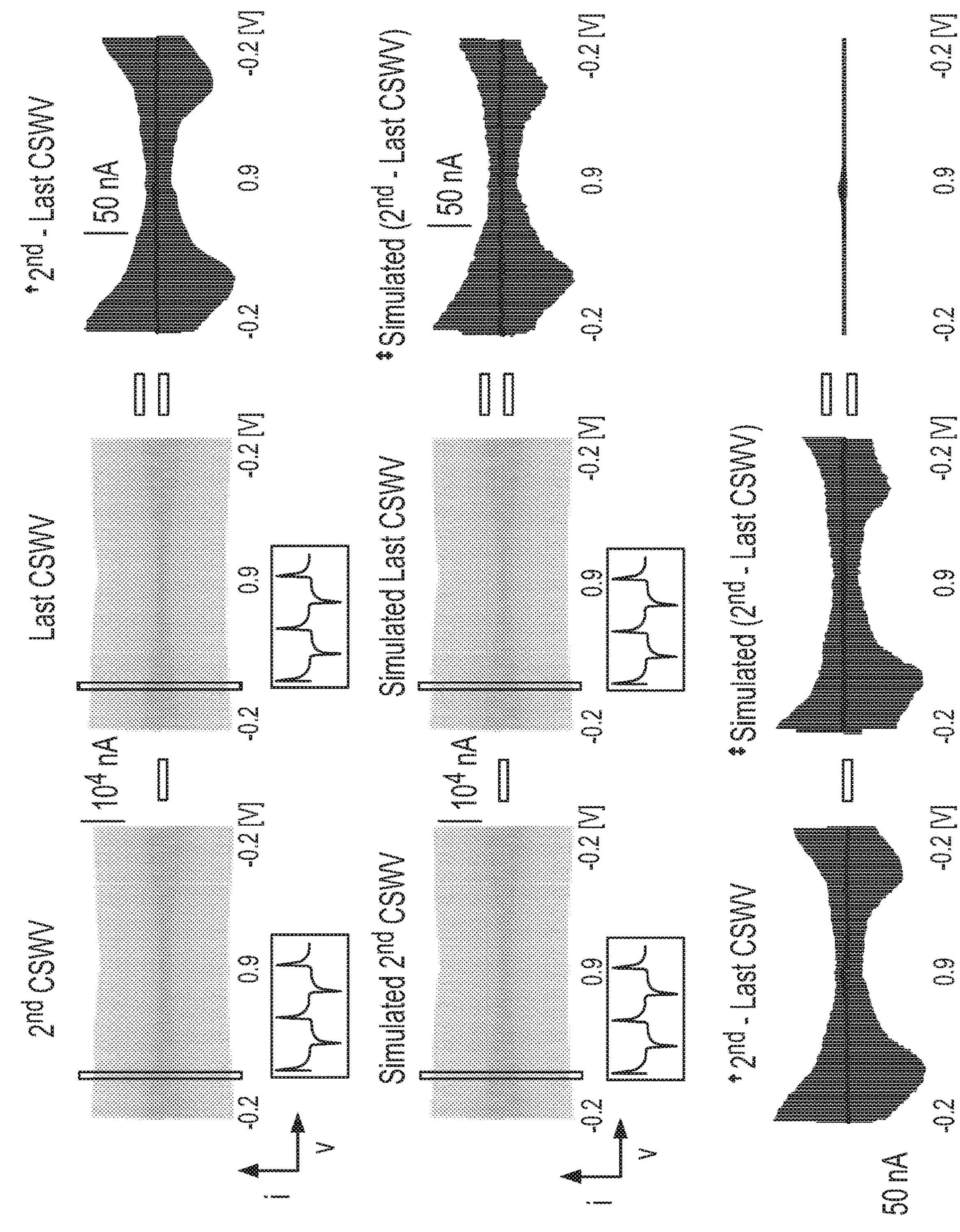

FIGS. 8A-8C depicts capacitive current response of M-CSWV and its modelling. FIG. 8A: The background current and its difference between 2nd and last CSWV. FIG. 8B: Modelled 2nd and last CSWV background current and its difference. FIG. 8C: Capacitive current removal by subtracting modelled CSWV from raw data.

Figure 9:
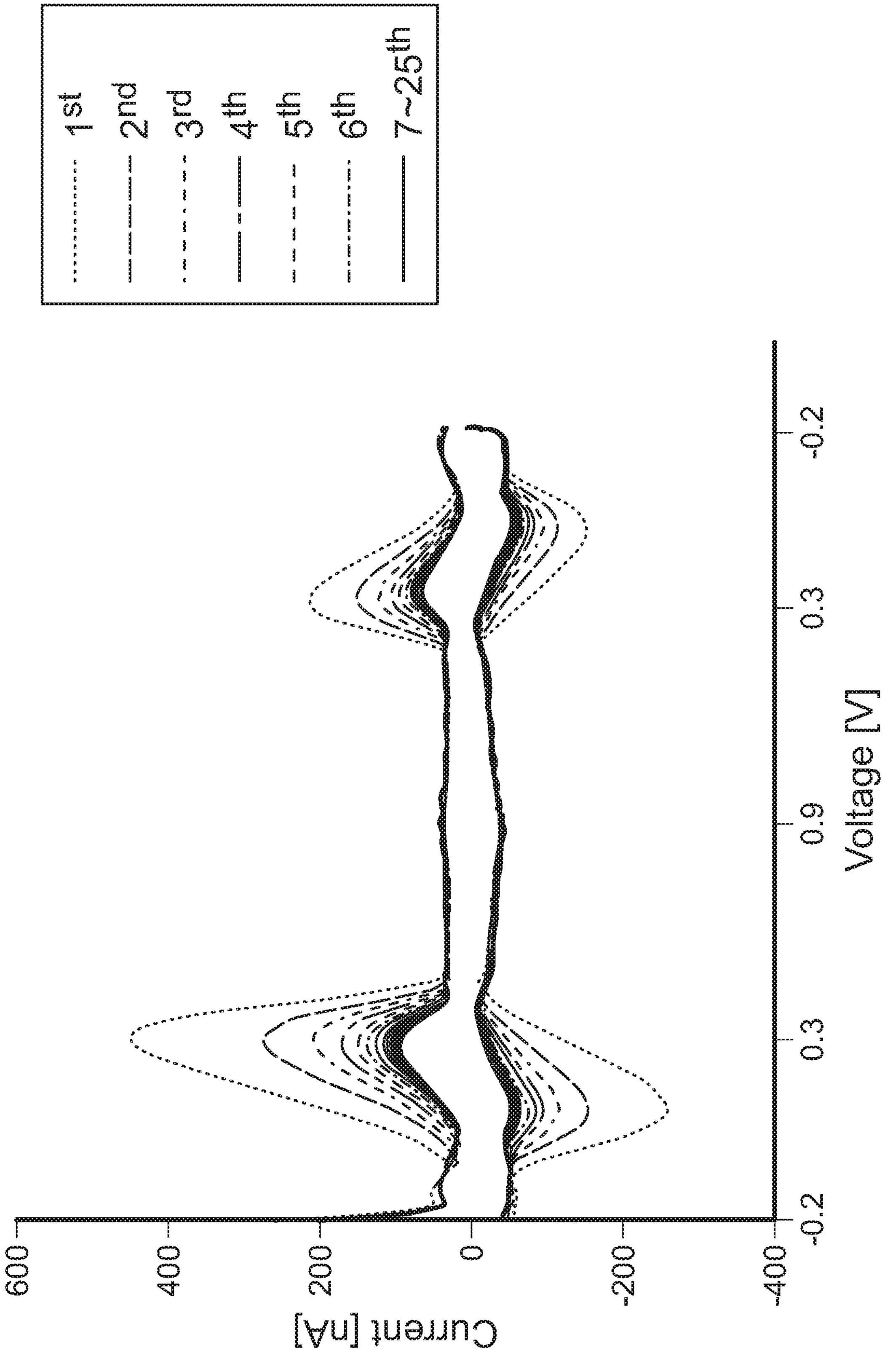

FIG. 9 depicts envelopes of DA responses. 25 cyclic square waveforms were used.

Figure 10:
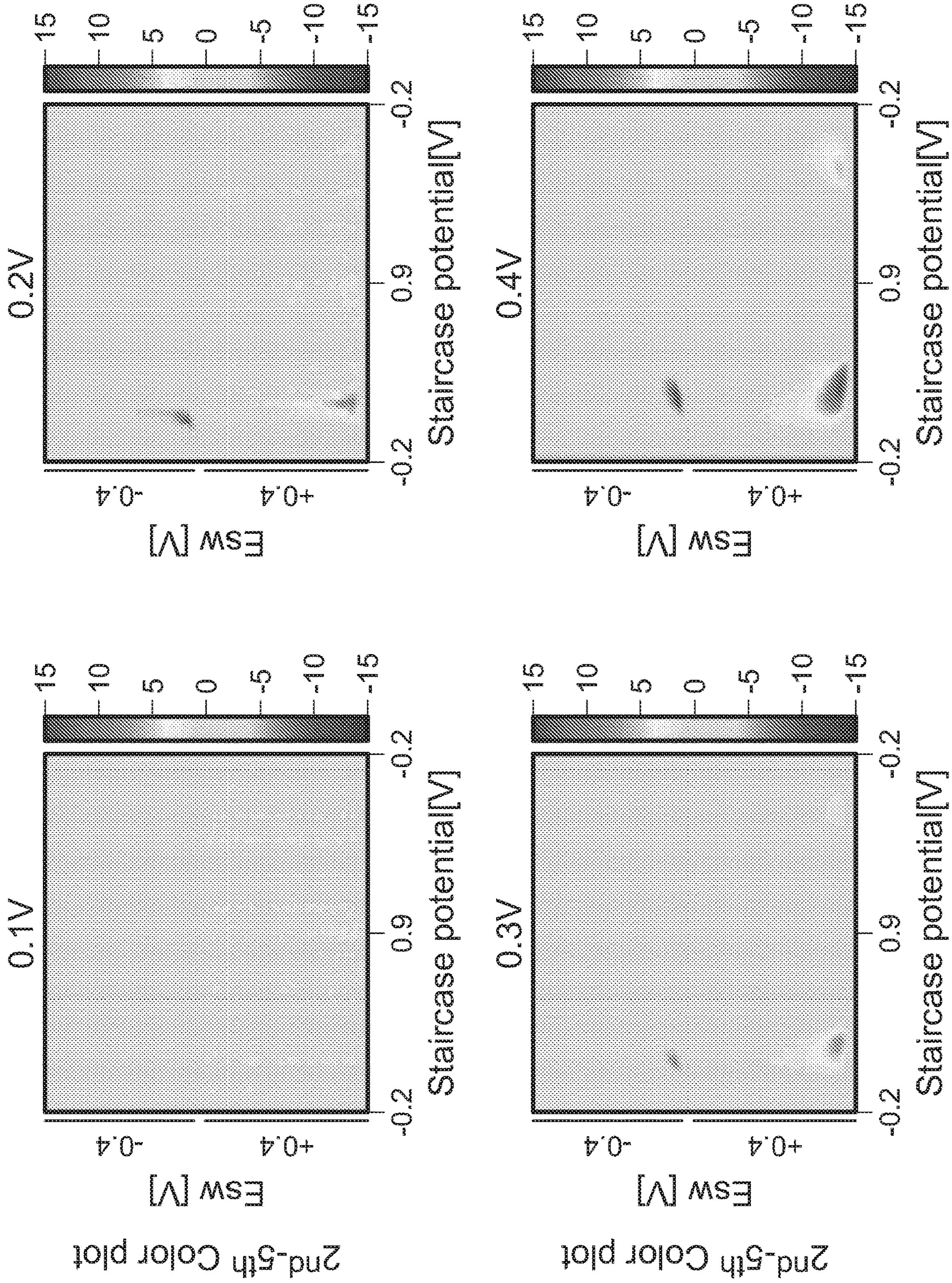

FIG. 10 depicts examples of $E_{SW}$ effect on the DA response.

Figure 11:
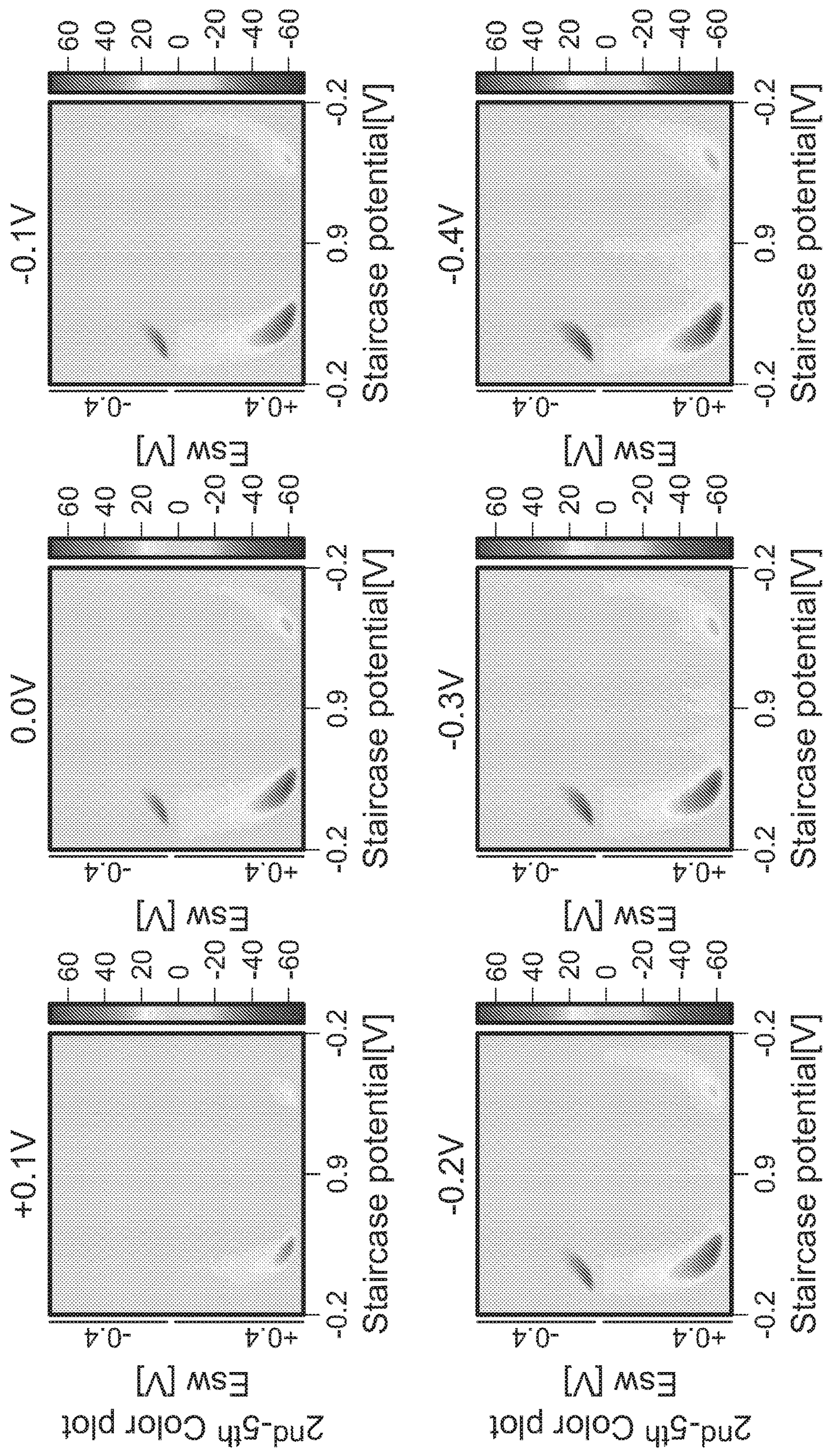

FIG. 11 depicts examples of $E_{Holding}$ effect on the DA response.

Figure 12A:
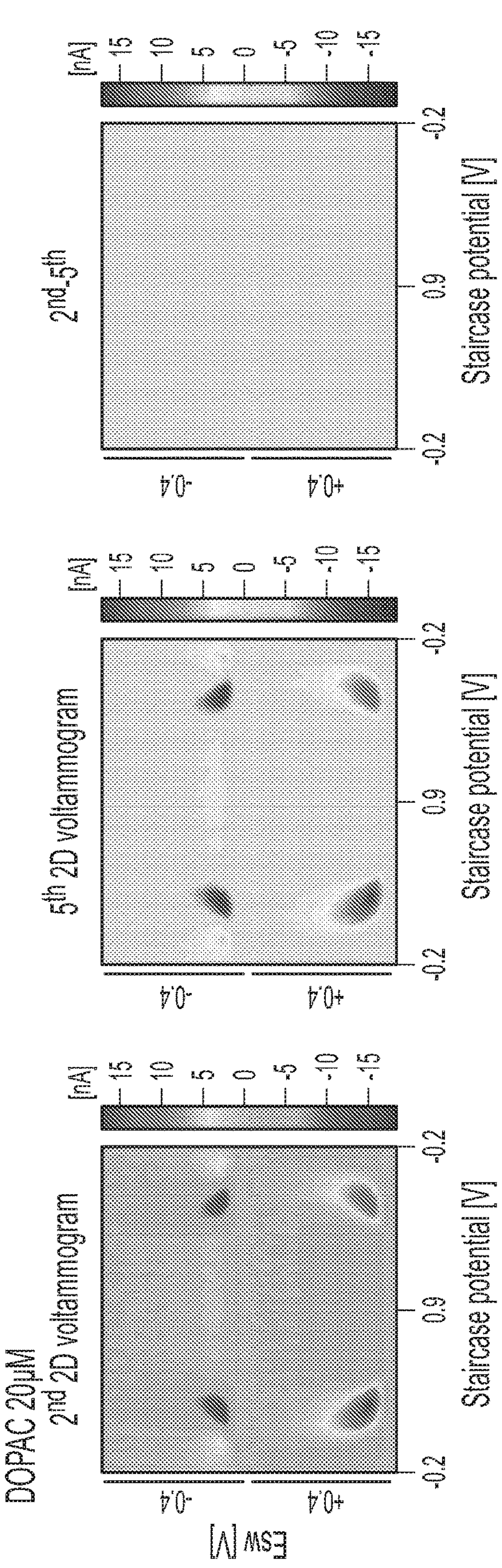
Figure 12B:
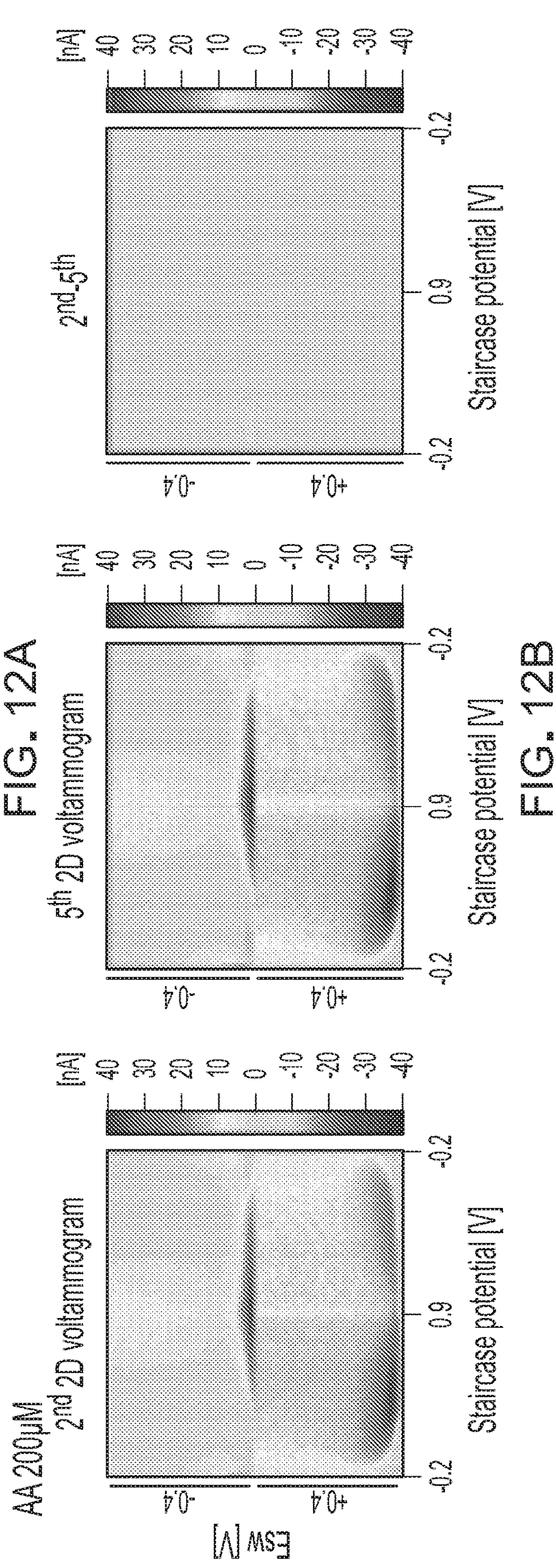
Figure 12C:
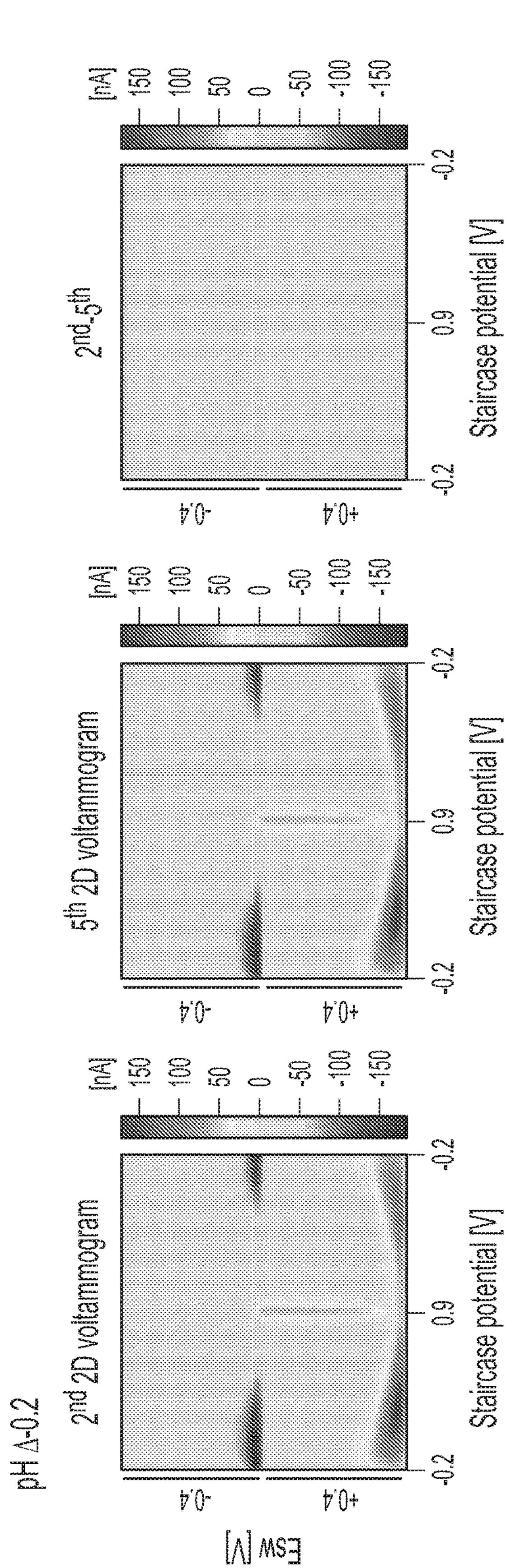

FIG. 12A-12C depict representative background-subtracted M-CSWV responses of DOPAC, AA, and pH change. FIG. 12A: Representative background-subtracted 2D voltammograms of 2004 DOPAC. DOPAC can be offset by subtracting 2nd and 5th CSWV. FIG. 12B: Representative background-subtracted 2D voltammograms of AA 200 μM. FIG. 12C: Representative background-subtracted 2D voltammograms of pH changes.

Figure 13A:
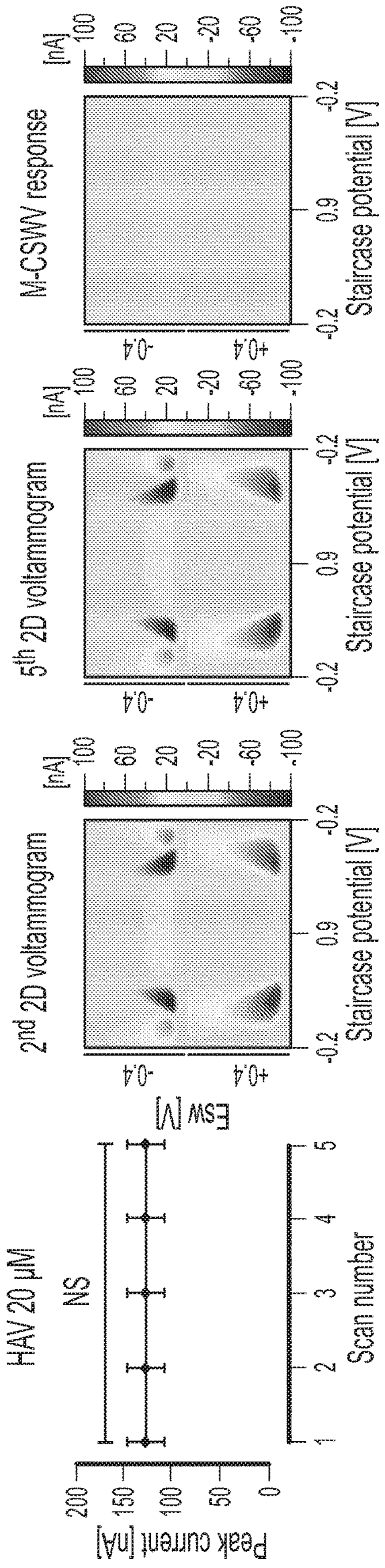
Figure 13B:
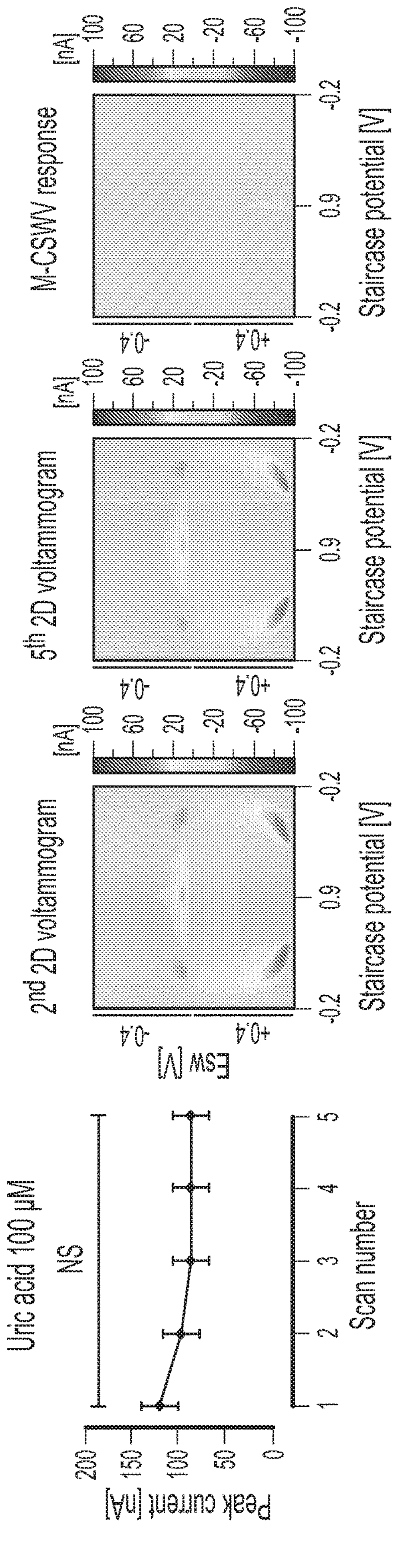
Figure 13C:
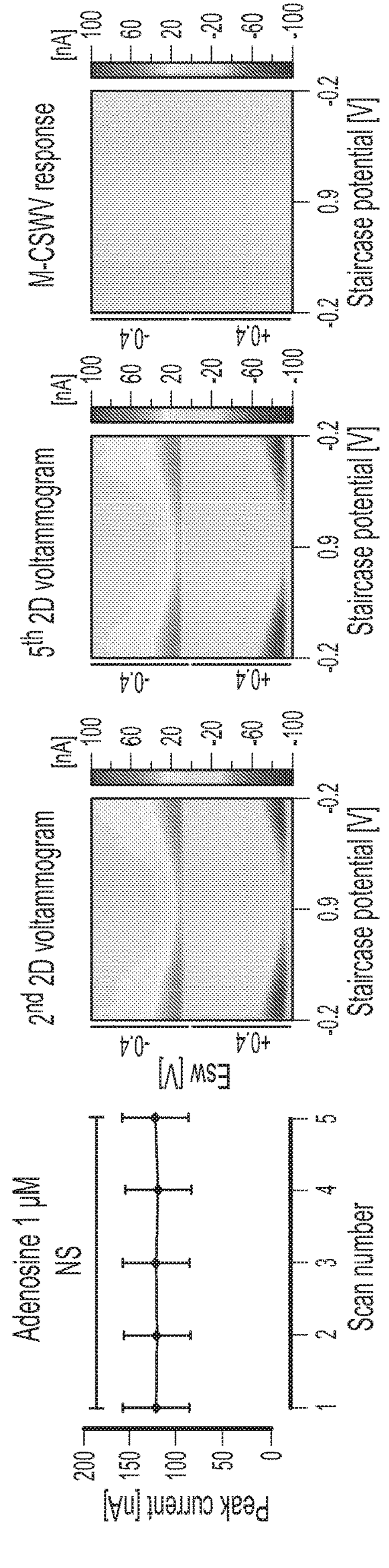

FIGS. 13A-13C depict representative background-subtracted M-CSWV responses for homovanillic acid (HVA), uric acid (UA), and adenosine. FIG. 13A: Peak oxidation currents of background-subtracted M-CSWV for HVA (20 μM). HVA responses from 1st to 5th CSWV showed no significant differences (n=3, one-way ANOVA test, left panel). Representative background-subtracted 2D voltammograms of 20 μM HVA (middle two pseudo color plots). HVA can be offset by subtracting 2nd and 5th CSWV (right panel). FIG. 13B: Uric acid (100 μM) responses from 1st to 5th CSWV showed no significant differences (n=3, one-way ANOVA test, left panel). Representative background-subtracted 2D voltammograms of Uric acid. FIG. 13C: Adenosine (1 μM) responses from 1st to 5th CSWV showed no significant differences (n=3, one-way ANOVA test, left panel). Representative background-subtracted 2D voltammograms of adenosine.

Figure 14A:
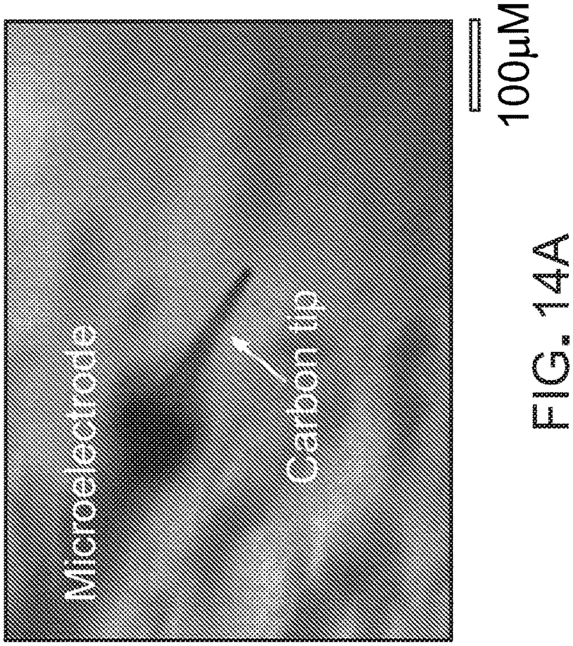
Figure 14B:
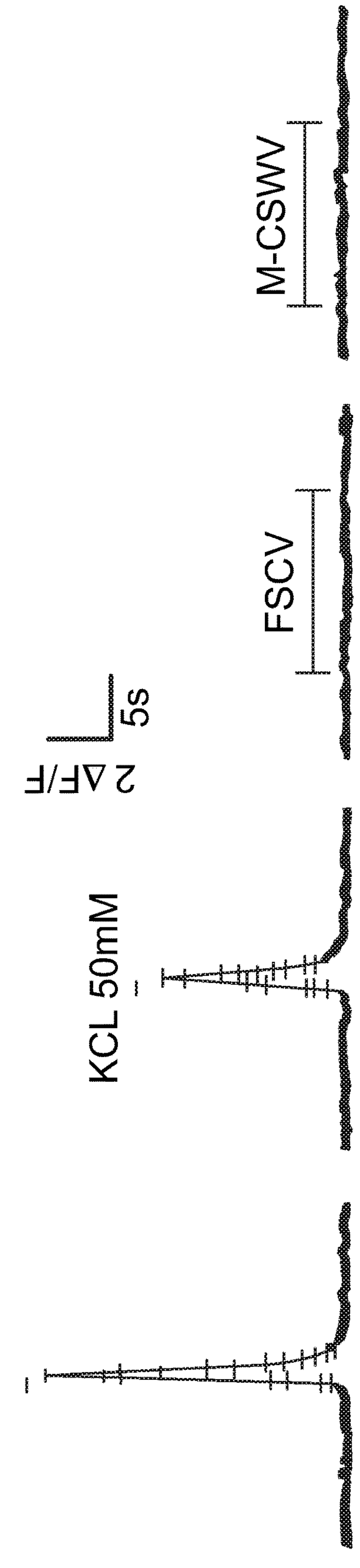

FIG. 14A-14B depicts in vivo feasibility test using brain slice of mouse. FIG. 14A: CFM placement in the brain tissue. FIG. 14B: Fluo-3 changes during experiments.

FIG. 15 is a table showing comparison of different techniques for the determination of tonic dopamine levels in rat brain.

Figure 16:
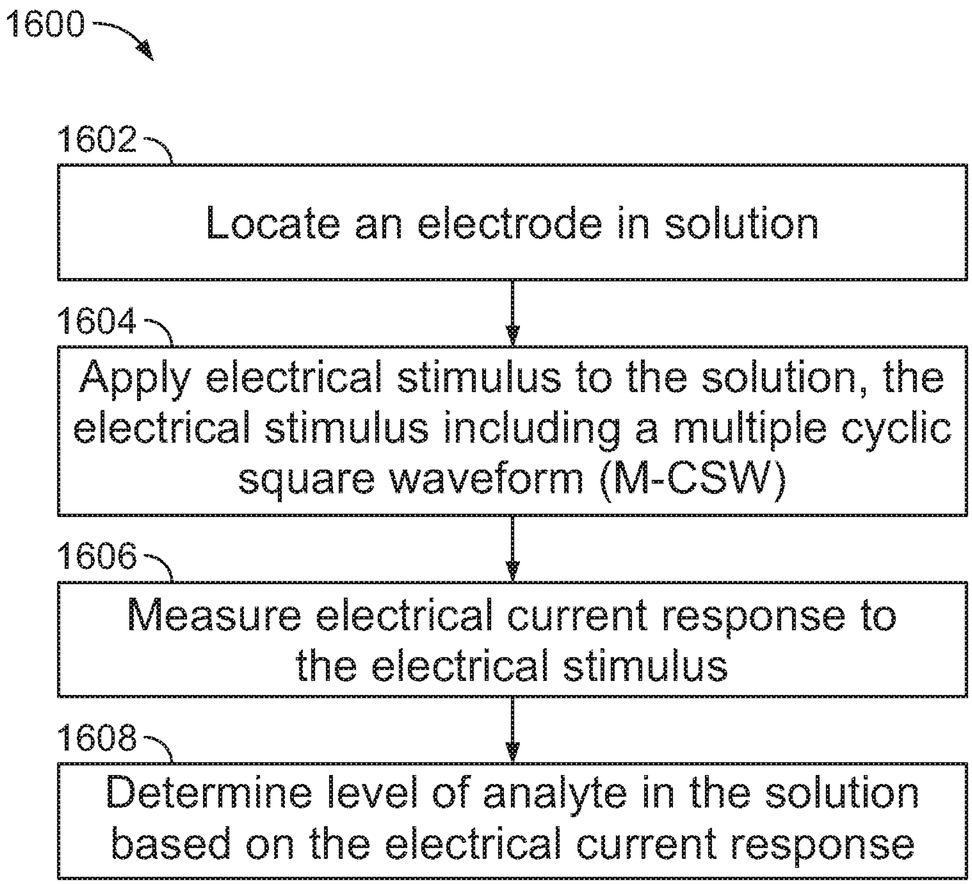

FIG. 16 depicts a flowchart of an example process for determining a level of an analyte in a solution using M-CSWV.

Figure 17:
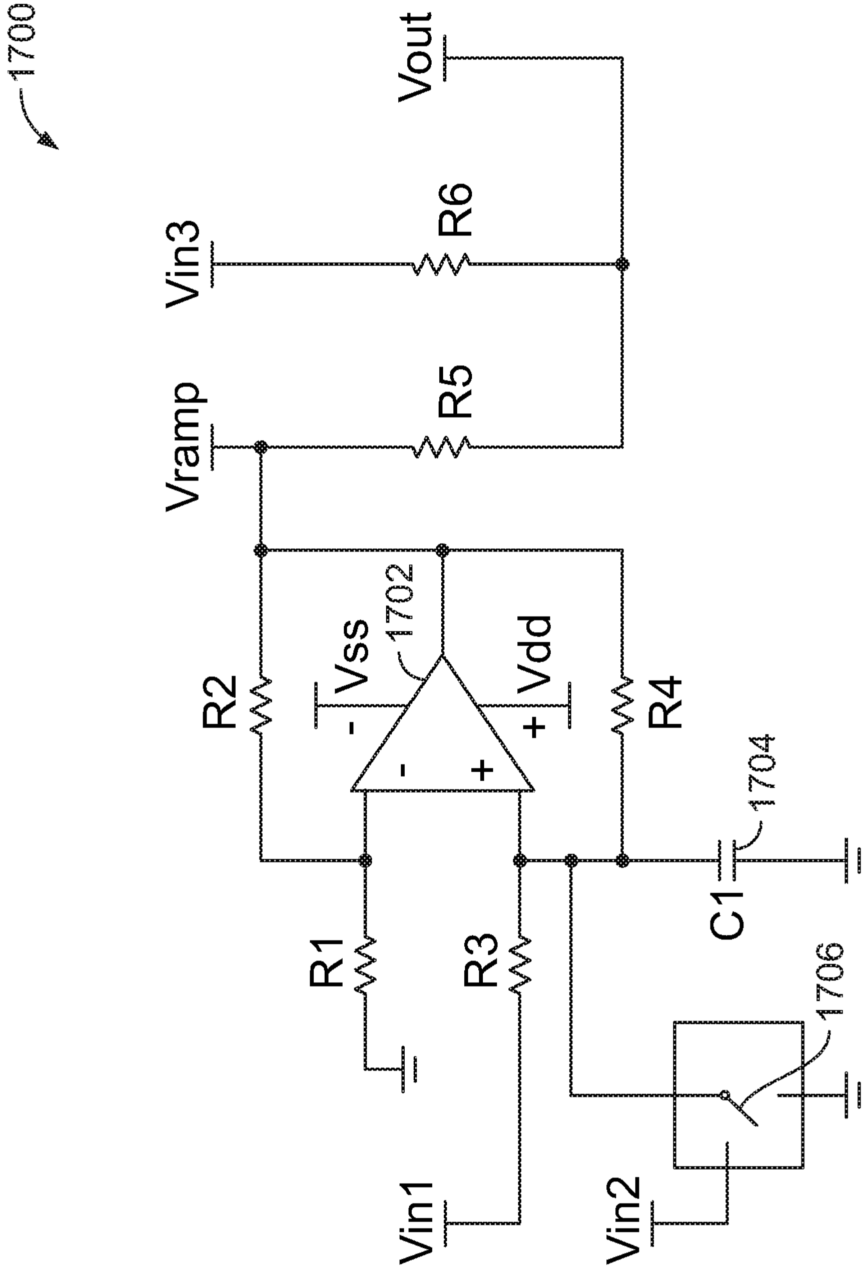

FIG. 17 depicts a circuit schematic for a Howland Integrator with summing circuitry.

Figure 18:
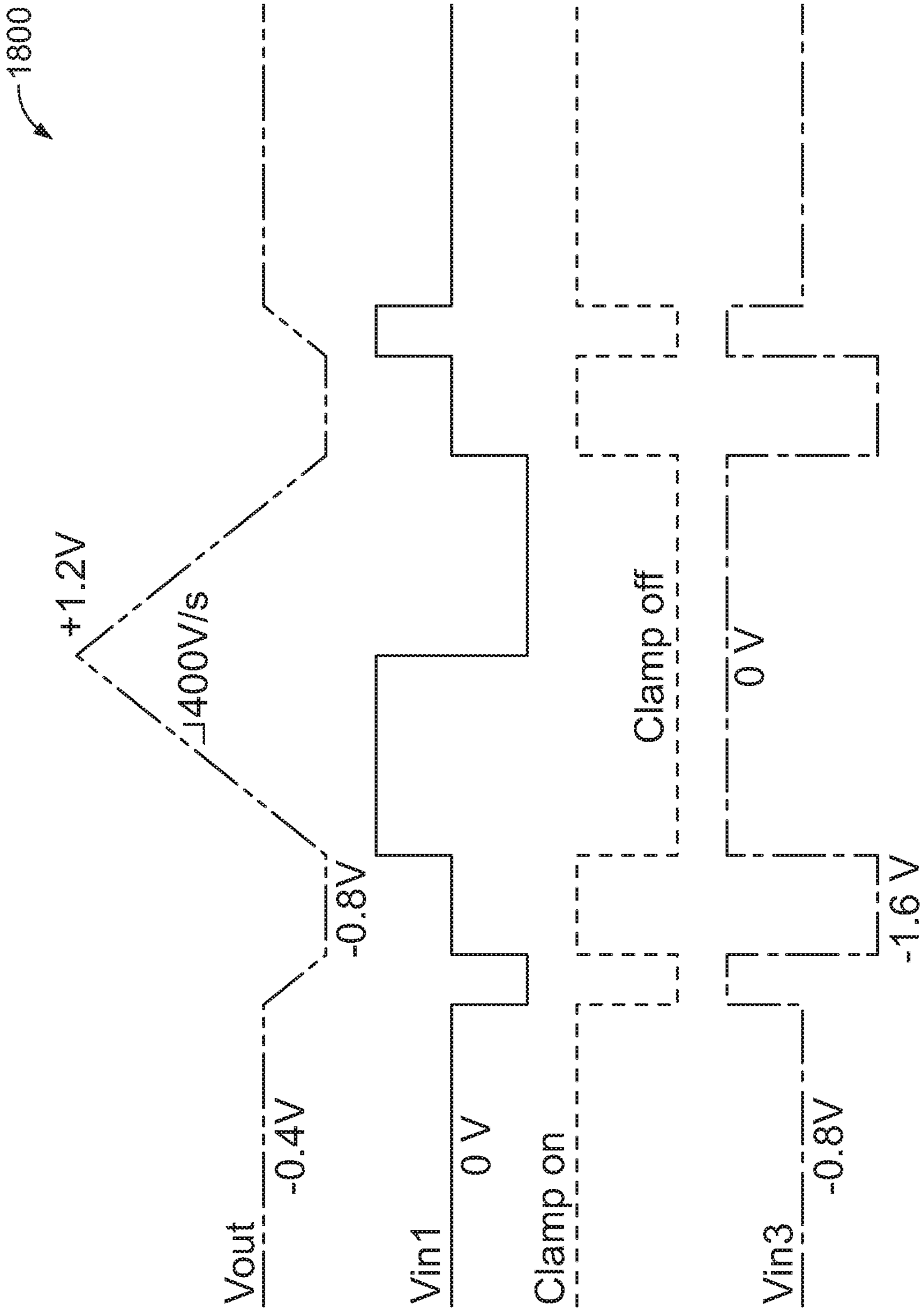

FIG. 18 depicts timing plots for a segmented fast-scan cyclic voltammetry (FSCV) waveform. The figure spans ~30 ms. In this instance, C1 is clamped to 0 V during all constant-voltage intervals of $V_{out}$.

Figure 19:
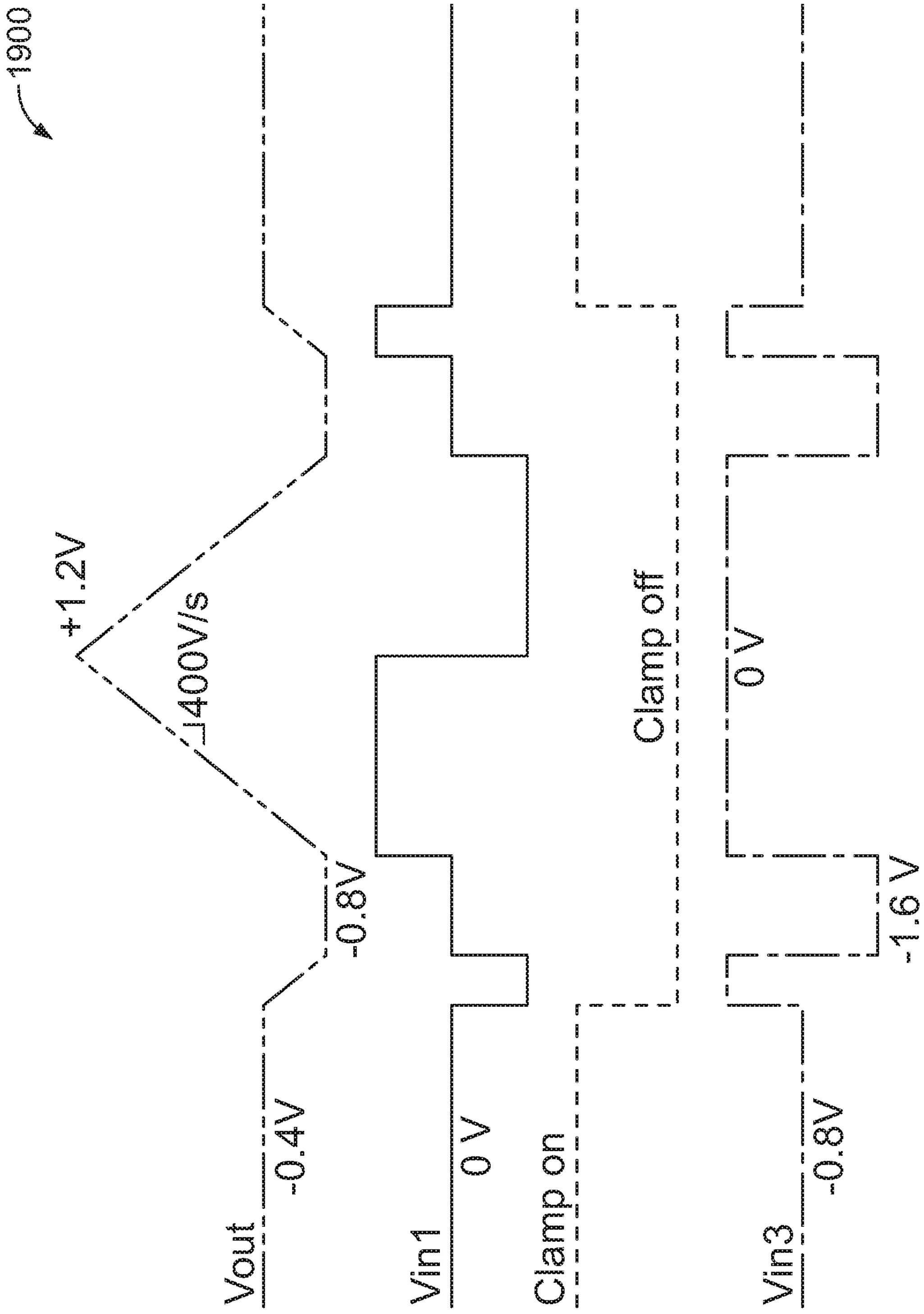

FIG. 19 depicts timing plots for a segmented FSCV waveform, produced with C1 unclamped during the short (~2 ms) constant-voltage intervals, as well as during all sloped segments.

Figure 20:
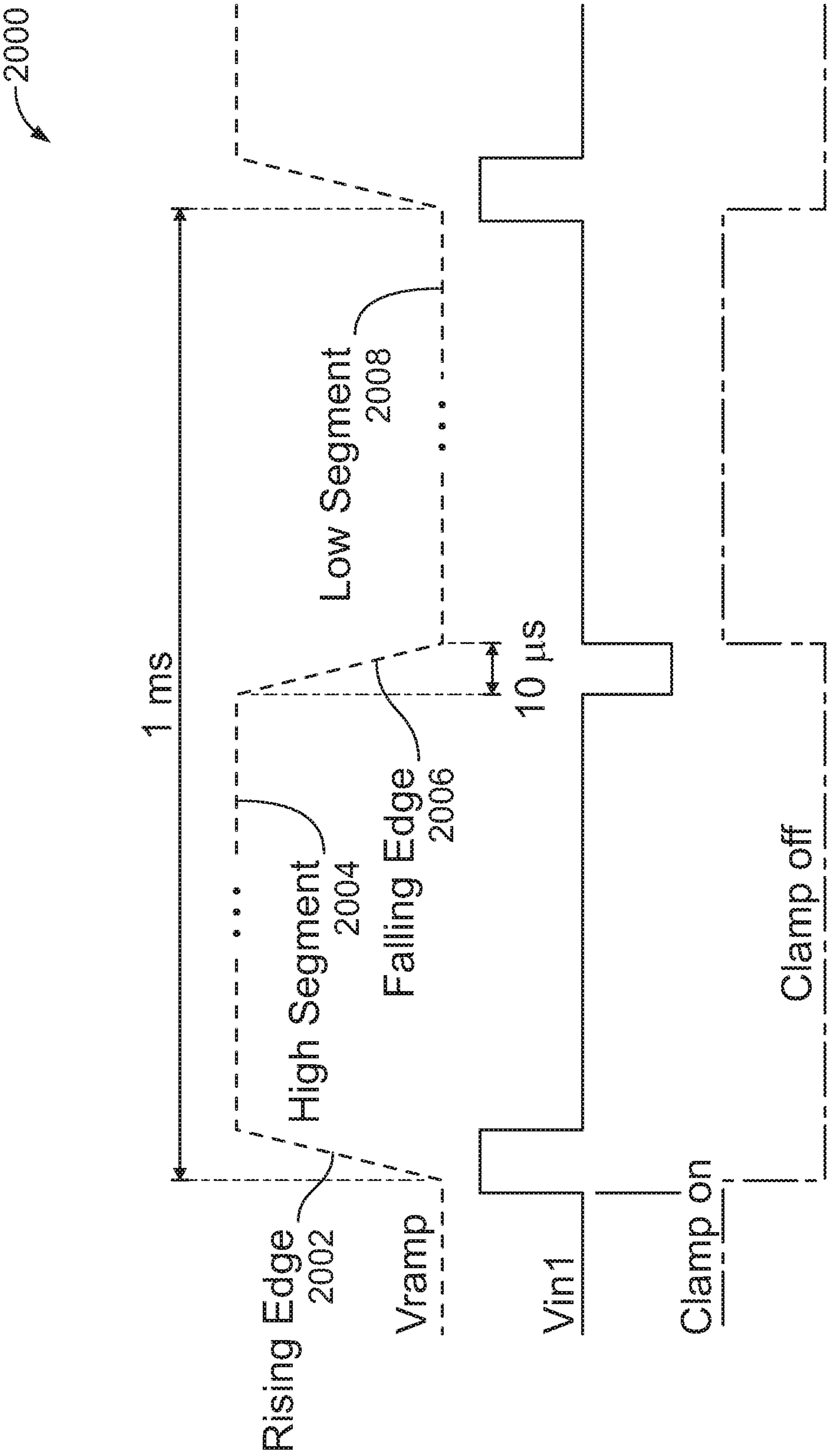

FIG. 20 depicts timing plots for the square-wave component of an M-CSWV waveform with sloped rising and falling edges. $V_{in1}$ is set for a positive slope while C1 is still clamped, just prior to the rising edge. The transition to the falling edge is made without engaging the clamp. To prevent error accumulation, C1 is clamped during the 'bottom' half of each square wave period.

Figure 21:
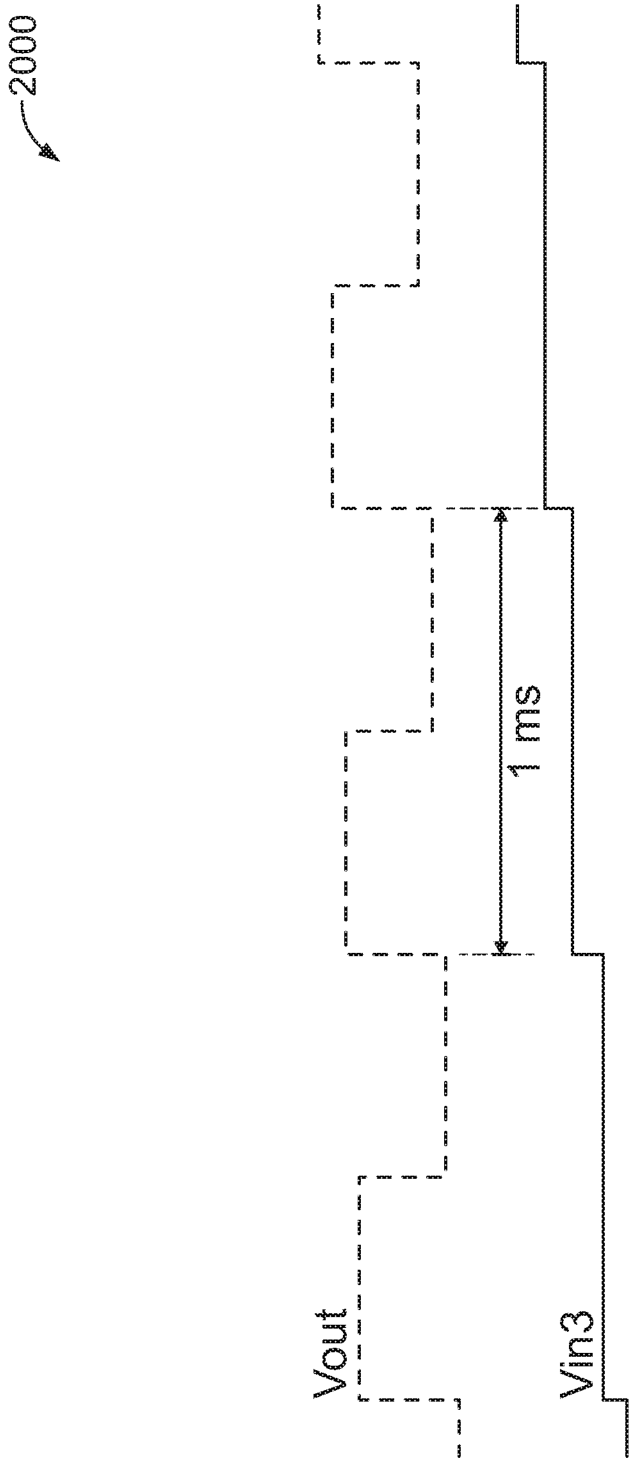

FIG. 21 depicts timing plots for the ascending half of the staircase waveform component of the M-CSWV "chevron" waveform. $V_{in3}$ is incremented by 50 mV each square wave period and summed with the $V_{ramp}$ square wave. The resulting increment in the chevron waveform is 25 mV. The $V_{in3}$ staircase goes down during the descending half of the M-CSWV waveform.

Figure 22:
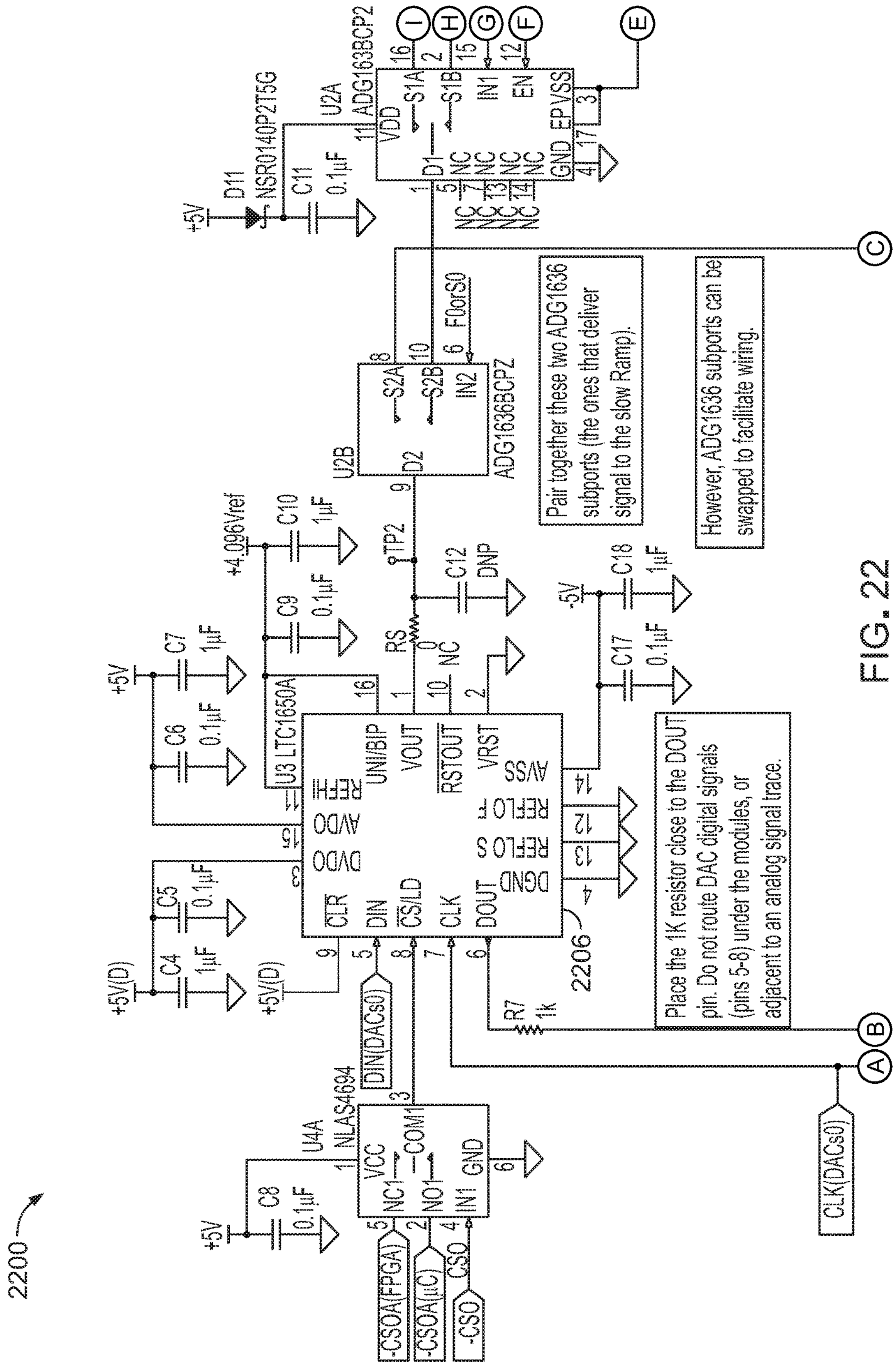
Figure 22:
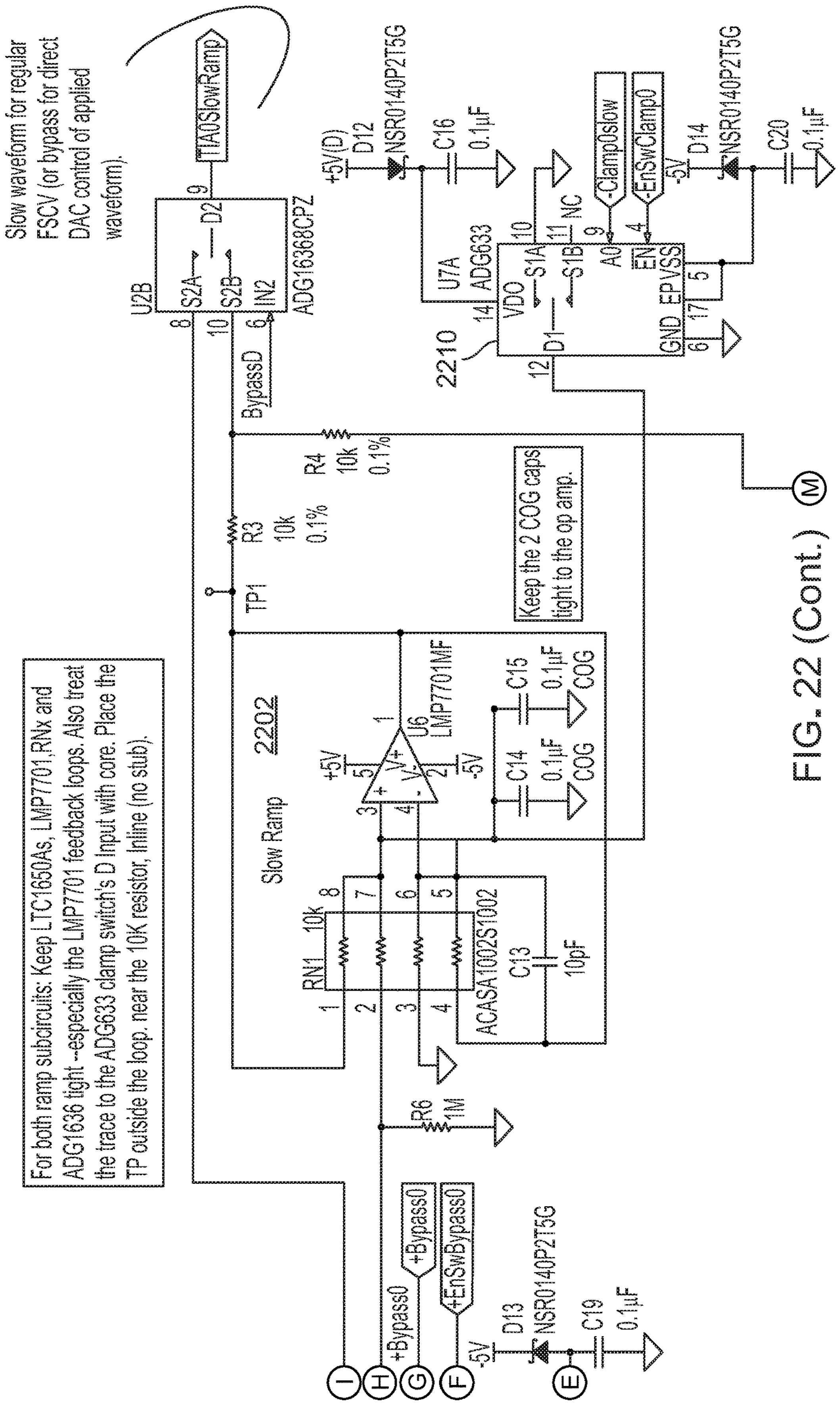
Figure 22:
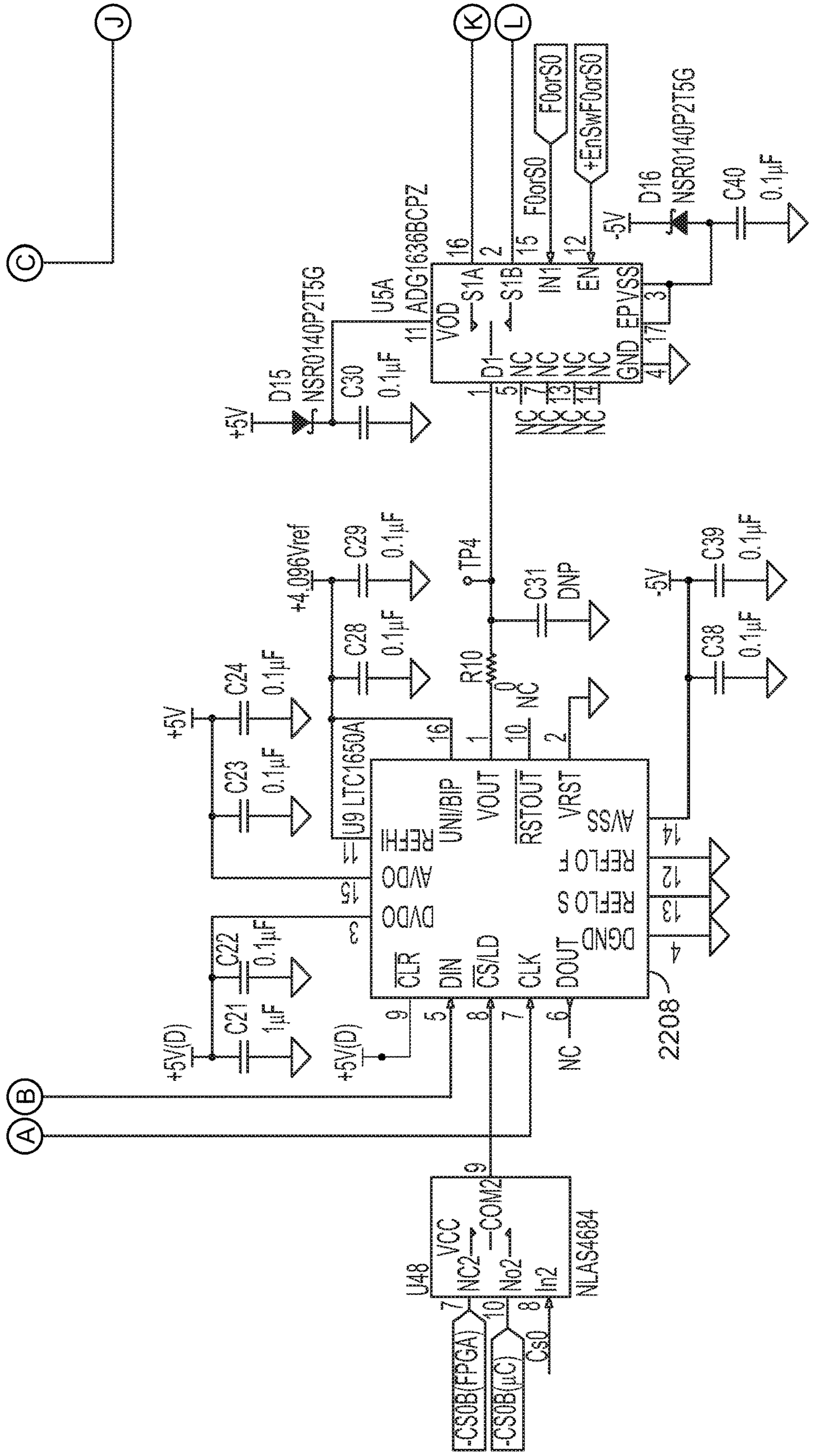
Figure 22:
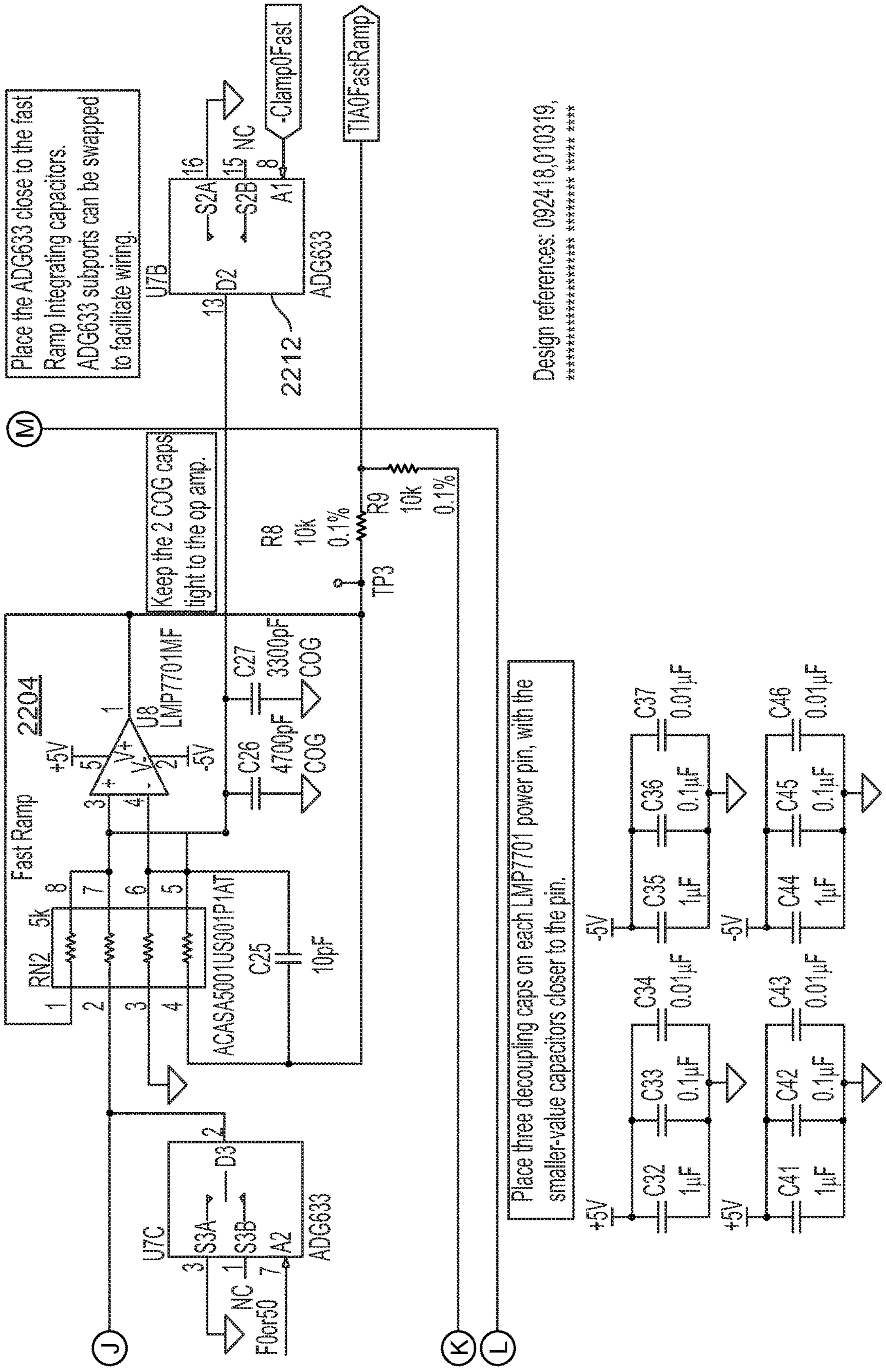

FIG. 22 depicts a schematic diagram of a waveform generation circuit 2200 for a voltammetric system.

Figure 23:
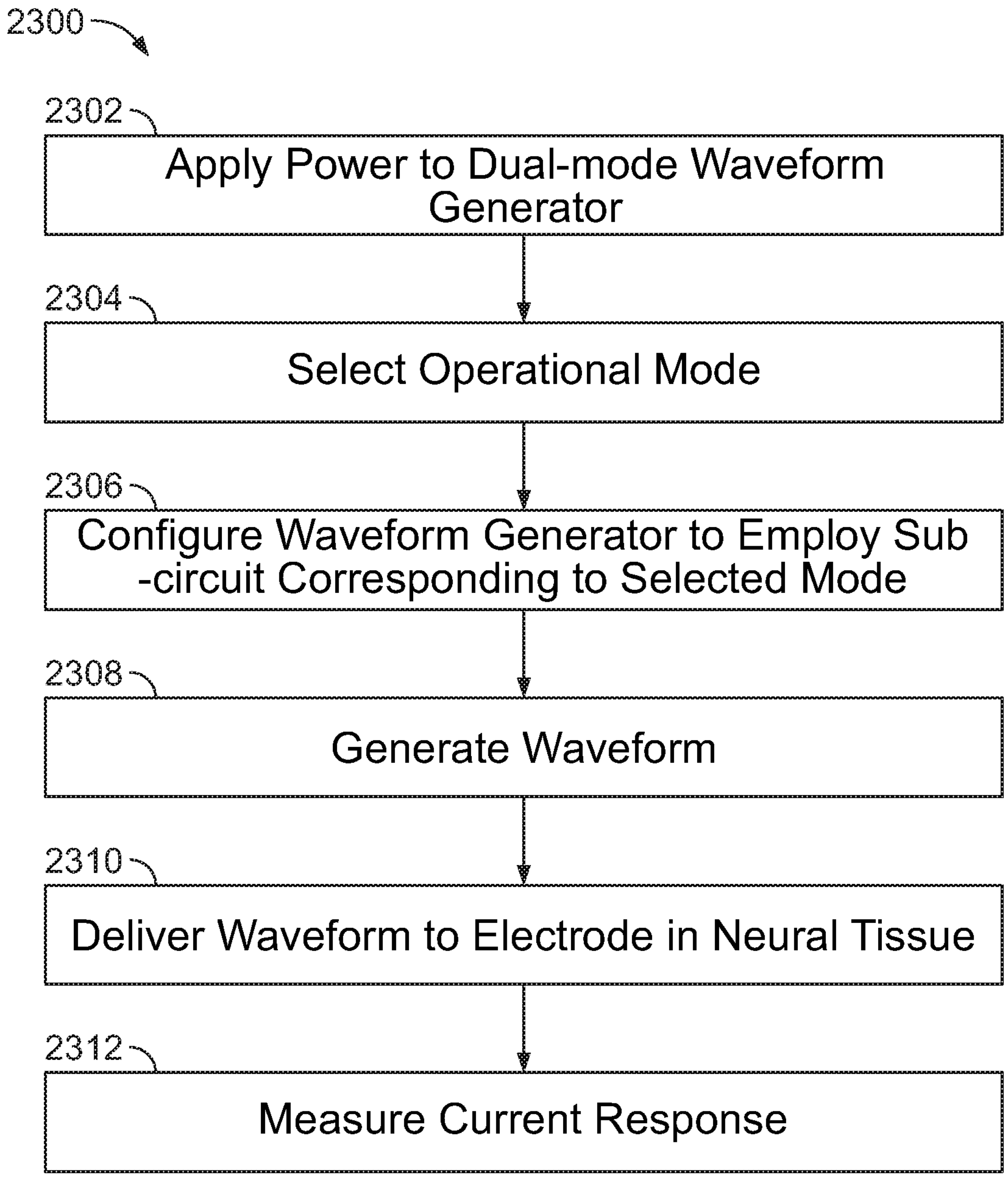

FIG. 23 depicts a flowchart of an example process for using a multi-mode waveform generator to perform voltammetry in a solution.

Figure 24:
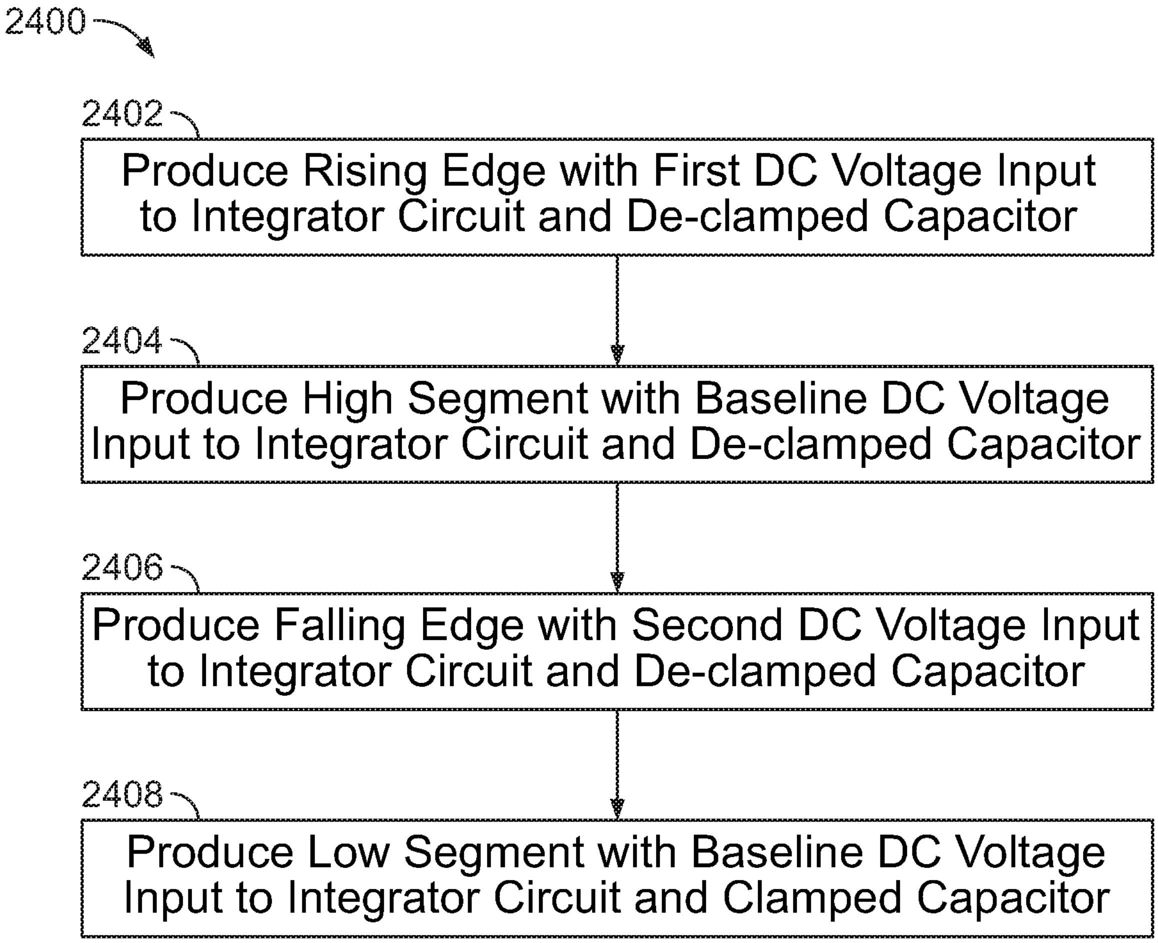

FIG. 24 depicts a flowchart of an example process for generating a sloped-edge square waveform.

DETAILED DESCRIPTION

This specification discloses systems, methods, devices, and other techniques involving application of multiple cyclic square wave voltammetry (M-CSWV) for analytical quantification of analytes in a solution. In some implementations, M-CSWV can be applied to measure tonic levels of dopamine in the brain of a mammal.

Performance of M-CSWV can include locating an electrode in a solution, applying a multiple cyclic square waveform electrical stimulus to the solution, measuring an electrical current response to the electrical stimulus using the electrode that is located in the solution, and determining a level of an analyte (e.g., dopamine) in the solution based on the electrical current response to the electrical stimulus.

Example Implementation #1

Materials and Methods

Data Collection and Analysis

In this example, multiple cyclic square wave voltammetry was performed using a commercial electronic interface (NI USB-6363, NATIONAL INSTRUMENTS) with a base-station PC and software written in-house using LABVIEW 2016 (NATIONAL INSTRUMENTS, Austin, TX). Data, in the form of a sequence of unsigned 2-byte integers, were saved to the base-station computer and processed by MATLAB (MATHWORKS INC., Natick, MA). The processing includes temporal averaging, filtering, and simulating background currents. GRAPHPAD PRISM 5 (GRAPHPAD SOFTWARE, San Diego, CA) was used to generate figures and perform statistics (one-way, two-way ANOVA with multiple comparisons, etc.). All data are presented as mean±standard error of the mean (SEM) values for n number of electrodes or rats.

Analysis of Dopamine Response to M-CSWV

A "dopamine-kernel" method was developed to extract the dopamine-featured response from M-CSWV. To make a dopamine-kernel, the dopamine oxidative response of M-CSWV was used and a threshold algorithm was applied where signals greater than 60% of the maximum oxidation current amplitude were assigned a value of one in the dopamine-kernel. A dopamine-kernel, K, was then applied to the dopamine response of M-CSWV, by multiplying each element of dopamine-kernel, kij, to a corresponding element of the M-CSWV response, $v_{ij}$.

$$K \odot V = k_{ij} \times v_{ij} | \in [1, \ldots, n] \text{ and } j \in [1, \ldots, m]$$

where i and j are the index of row and column respectively, and K and V have the same matrix size (n×m). For each CFM, the dopamine-kernel was determined from in vitro dopamine experiments and applied to analyse in vivo data.

Carbon-Fiber Microelectrode (CFMs)

Each CFM was fabricated by isolating and inserting a single carbon fiber (AS4, d=7 μm; HEXEL, Dublin, CA) into a silica tubing (20 μM ID, 90 μM OD, 10 μM coat with polyimide; POLYMICRO TECHNOLOGIES, Phoenix, AZ). The connection between the carbon fiber and the silica tubing was covered with polyamic acid (SIGMA-ALDRICH, St. Louis, MO) and heated to 200° C. to polymerize the polyamic acid into a polyimide film. The silica tubing was then attached to a nitinol (Nitinol #1, an alloy of nickel and titanium; FORT WAYNE METALS, IN) extension wire with a silver-based conductive pastel. The carbon fiber attached nitinol wire was insulated with polyimide tubing (0.00891D, 0.0134"OD, 0.00225" WT; VENTION MEDICAL, Salem, NH) except the carbon fiber sensing part. The exposed carbon fiber was trimmed under a dissecting microscope to a length of approximately 50 μm. Teflon-coated silver wire (A-M SYSTEMS, INC., Sequim, WA) was prepared as an Ag/AgCl reference electrode and chlorinating the exposed tip in saline with a 9 V dry cell battery.

AS4 carbon fiber (HEXEL, Stamford, CT) was used for all experiments in this example. The exposed carbon fiber was trimmed to approximately 50 μm in length, then PEDOT:nafion coating was applied onto the exposed carbon fiber for all electrodes. The microelectrodes were dried overnight at room temperature.

Chemicals

Dopamine HCl, DOPAC, and AA were dissolved in distilled water at a stock concentration of 1 mM, 10 mM, and 100 mM, respectively, and preserved in 0.1 M perchloric acid. Samples from the stock solutions were diluted with TRIS buffer (15 mM tris, 3.25 mM KCl, 140 mM NaCl, 1.2 mM $CaCl_2$, 1.25 mM $NaH_2PO_4$, 1.2 mM $MgCl_2$, and 2.0 mM $Na_2SO_4$, with the pH adjusted to 7.4) for desired concentration. All chemicals, including nomifensine maleate salt and pargyline HCl, were purchased from SIGMA-ALDRICH (St. Louis, MO).

Preparation of Brain Slices for $Ca^{2+}$ Imaging

Mouse striatum slice preparation and $Ca^{2+}$ imaging experimental procedures were performed according to NIH guidelines and approved by the Hanyang University Institutional Animal Care and Use Committee.

After rapid extraction of mouse brain, 300 μM horizontal striatum slices were prepared using a Vibratome 1000 (THE VIBRATOME COMPANY, St. Louis, MO). After a minimum period of 60 to 90 minutes, the slices were continuously perfused with oxygenated artificial cerebrospinal fluid solution (28-30° C.) (in mM; NaCl 125, KCl 2.5, $CaCl_2$ 2, $NaHCO_3$26, $NaH_2PO_4$ 1.25, $MgCl_2$ 1, glucose 25, pH 7.4 when bubbled with 95% 02 and 5% $CO_2$) in a submersion-type recording chamber. In $Ca^{2+}$ image analysis, $Ca^{2+}$ response of striatal neurons was measured using the fluorescent $Ca^{2+}$ probe (indicator) Fluo-3 AM (10 mM, Enzo Life Science, Farmingdale, NY) mixed with 1 ml pluronic acid (20% solution in DMSO, Life Technologies) in DMEM medium (with 10% FBS) for 40 min at 3TC. Fluo-3 loaded slices on coverslip were mounted onto the chamber (12 mm Chamlide AC, total volume of 500 ul, Live Cell Instrument, Korea), and placed onto an inverted microscope (Olympus IX70, Japan). Cells were excited with a LED source pE-100 (CoolLED, UK) at 470 nm and emissions were recorded at 535 nm wavelengths, Fluorescent emission readings were recorded and stored on hard disk every 0.5 s. Intracellular concentrations ($[Ca^{2+}]_i$) were measured by digital video microfluorometry with an intensified charge-coupled-device (CCD) camera (QICLICK, QIMAGING, Canada) coupled to the microscope and a computer with software (METAMORPH® NX, MOLECULAR DEVICES). $Ca^{2+}$ responses were presented as a pseudo ratio (ΔF/F) to estimate comparison fluorescence intensity, because Fluo 3-AM is a non-ratiometric $Ca^{2+}$ indicator. Single-wavelength values are different depending on the concentration of loaded dye in respective cells. Following formula indicates pseudo ratio.[3]

$$\Delta F/F = (F_1 - F_{base})/F_{base}$$

$F_1$=measured intensity of the cell after stimulation $F_{base}$=measured intensity of the cell before stimulation In Vivo Experiments Adult male Sprague Dawley rats weighing 250-350 g were used for the in vivo experiments in these studies (n=5, each group). NIH guidelines were followed for all animal care, and the MAYO CLINIC Institutional Animal Care and Use Committee approved the experimental procedures. WINCS Harmoni was used to perform fast-scan cyclic voltammetry (FSCV) and electrical stimulation to identify dopamine releasing sites in the dorsomedial striatum. Once an optimal CFM recording site was identified, the device was changed to the M-CSWV recording system for tonic dopamine concentration recording.

Biological Experiments Protocol

Rats were housed with a 12:12 hr light and dark cycle (lights on at 0600 hr) with ad libitum access to food and water. The rats were anesthetized with an injection of urethane (1.6 g/kg, i.p.) and stabilized in a commercially available stereotaxic frame (DAVID KOPF INSTRUMENTS, Tujunga, CA) for the surgery. A longitudinal incision was made on the skin to expose the skull and three burr holes (0.5-1.0 mm diameter) were made in the skull of each rat for the implantation of a CFM, a bipolar electrical stimulating electrode (PLASTIC ONE, MS303/2, Roanoke, VA, USA) and an Ag/AgCl reference electrode. The reference electrode was positioned superficially in cortical tissue contralateral to the CFM and stimulating electrode. Electrode coordinates were referenced by a rat brain atlas based on flat-skull position using bregma and dura as reference points with coordinates anteroposterior (AP), mediolateral (ML), and dorsoventral (DV). The CFM was placed in the right hemisphere in the dorsomedial striatum (AP+1.0 mm; ML+2.5 mm; DV −4.5 to −5.5 mm), and the stimulating electrode was inserted ipsilaterally just above the medial forebrain bundle (MFB, AP −4.8; ML+1.0; DV −8.0 to −9.0). A train of bipolar pulses (2 ms pulse width, 200 μA, 60 Hz) using WINCS Harmoni electrometer was delivered for 2 seconds to identify dopamine releasing sites in the striatum. FSCV signal was synchronized with electrical stimulation in order to interleave intervals of stimulation during FSCV scans. Thus, electrical stimulation was not applied when the FSCV pulses (about 10 ms) were delivered. The CFM and the electrical stimulating electrode were gradually adjusted until a robust phasic DA signal was detected at the CFM using FSCV. Immediately thereafter, a M-CSWV waveform was applied at 0.1 Hz for ~10 minutes to allow stabilization of the recorded electrochemical signal. Striatal tonic DA levels were collected for one hour, then saline, 20 mg/kg nomifensine, or 75 mg/kg pargyline was injected i.p. and tonic DA levels were collected for additional 2 hours.

Results and Discussion

Multiple Cyclic Square Wave Voltammetry (M-CSWV)

The adsorption characteristics of dopamine on the CFM surface were leveraged to conduct M-CSWV. Relative to some other voltammetry techniques, M-CSWV can provide significantly higher temporal resolution (e.g., 10 seconds) and additional dimensional analysis in the voltammogram by using a modified form of cyclic square wave voltammetry.

Figures 1A, 1B, 1C:
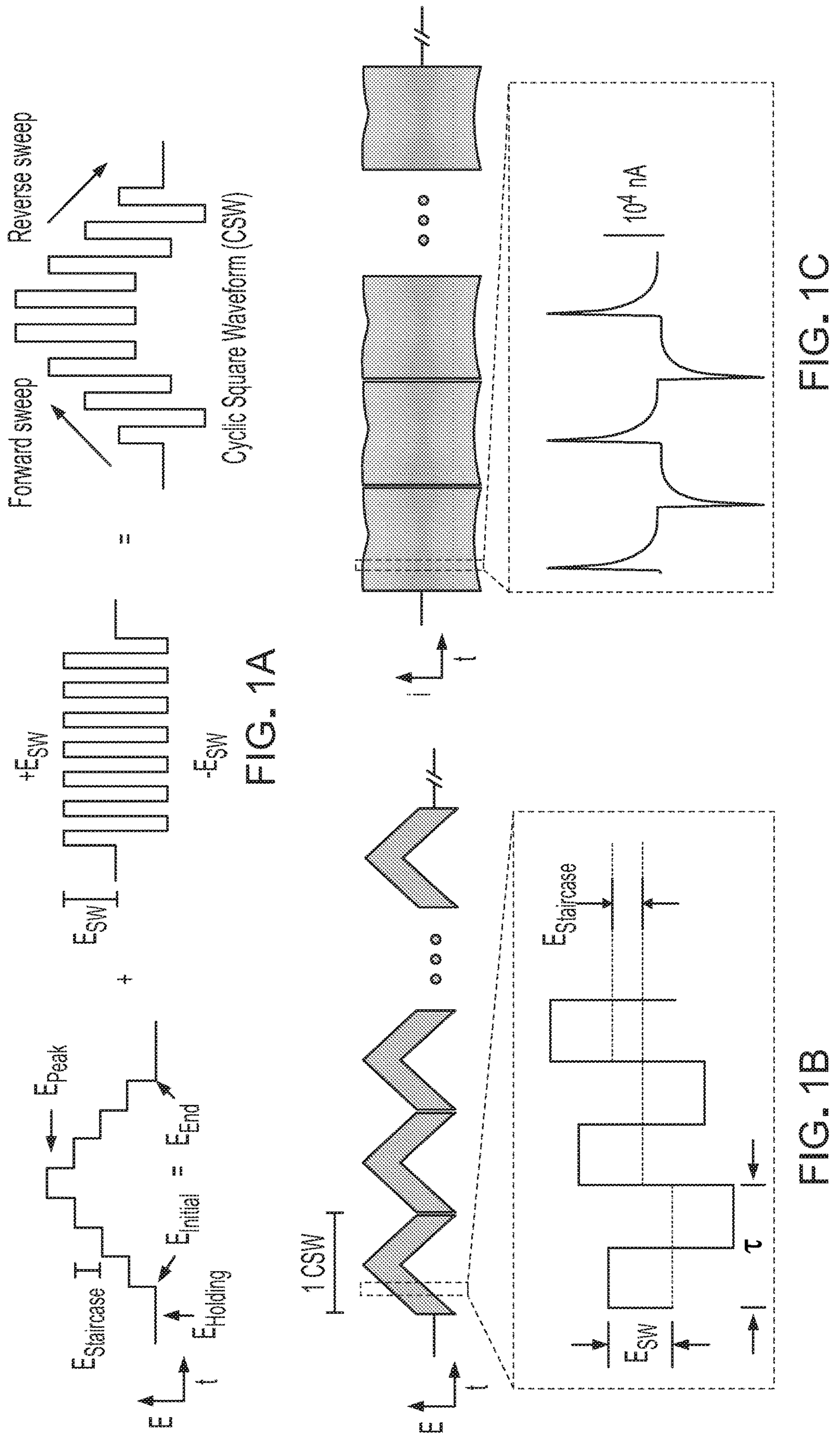
FIGS. 1A-1C illustrate the schematic design of multiple cyclic square wave voltammetry (M-CSWV).

FIG. 1 depicts waveforms applied and the current responses. The cyclic square waveform (CSW) is based on a square wave oscillation superimposed on a symmetric staircase waveform (FIG. 1A). In this example, CSWs were applied consecutively multiple times resulting in multiple cyclic square wave voltammetry, M-CSWV (FIG. 1B). This exploits the adsorption characteristics of dopamine at CFMs to enable measurements of tonic dopamine concentrations. The waveform parameters, $E_{staircase}$, $E_{Initial}$ (=$E_{End}$) and i were fixed at 25 mV, −200 mV and 1.0 ms, respectively. $E_{staircase}$ was maintained at 25 mV because it mainly determines the duration of CSW. If the $E_{staircase}$ is too large, the current response can be distorted by the potential steps; it is preferably dominated by $E_{SW}$ and not $E_{staircase}$. $E_{Initial}$ was set to −200 mV to avoid loss of the dopamine redox response to M-CSWV which empirically possess features at −400 mV (see below). The experiment was designed such that the combination of $E_{Initial}$ and $E_{SW}$ caused the potential spanning the redox potential of dopamine to be applied. Lastly, a τ of 1.0 ms was used to give each upward and downward potential sufficient time for the decay of capacitive charging currents to plateau (FIG. 1C). However, τ could not be too long since it also affects the length of CSW.

M-CSWV of Dopamine

Figures 2A, 2B, 2C:
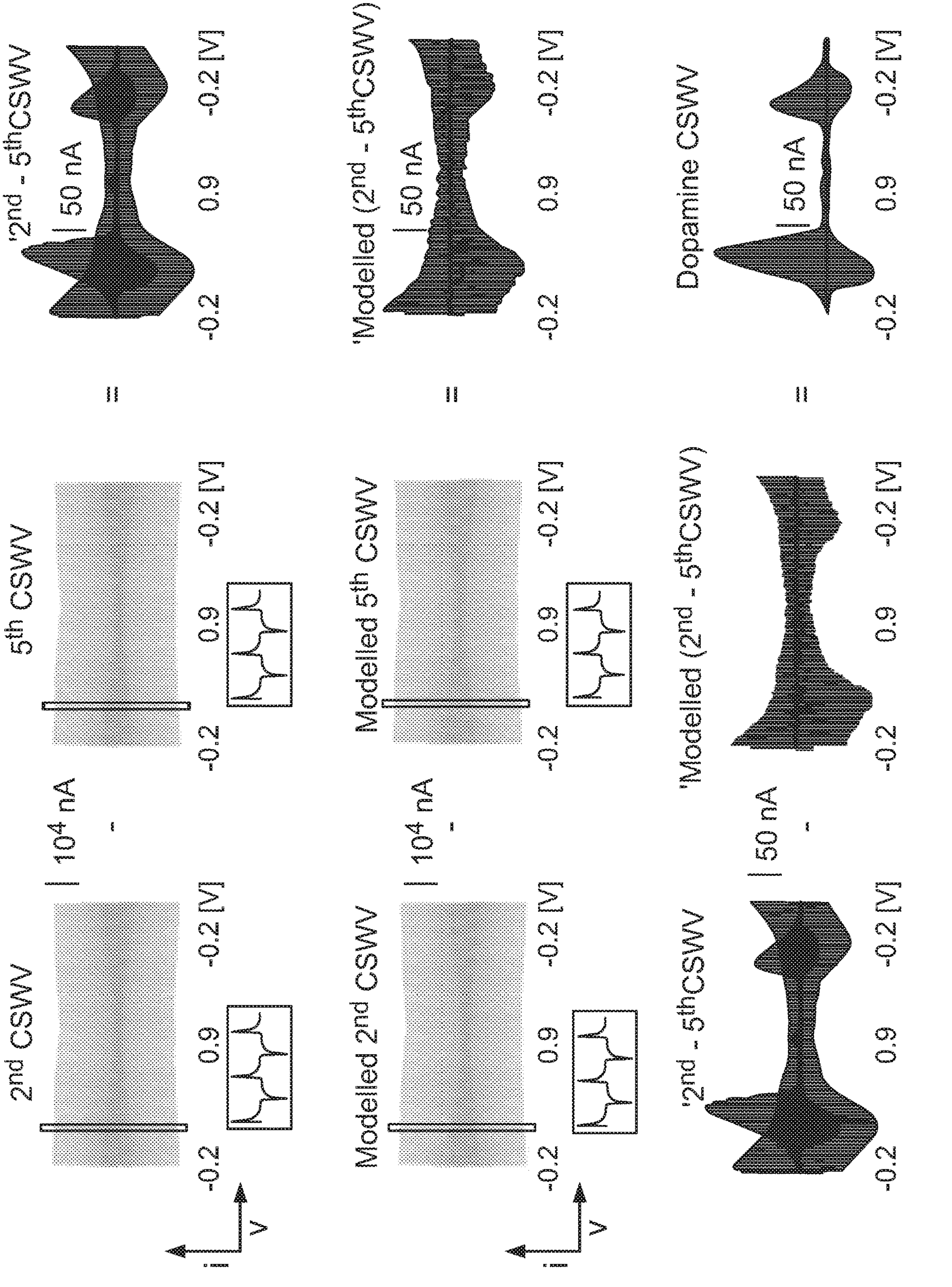
FIGS. 2A-2E illustrate M-CSWV response for 1 μM dopamine.

The M-CSWV with five CSWs responses to 1.0 μM of dopamine in TRIS buffer shows that this technique can measure tonic dopamine concentrations (FIG. 2). An example of the raw signal recorded from the CFM in a solution of dopamine is shown in FIG. 2A. The signal has two components, a large capacitive charging current and faradaic current due to the dopamine redox reaction at both forward and reverse sweeps. Because the amount of dopamine decreases as successive CSWs are applied, the fifth CSW was subtracted from the second CSW to reveal the difference in the signal. The second CSW was chosen for better selectivity performance as discussed below. Note the result after subtraction is ~100 times smaller than the raw signal. The dopamine redox pattern was still present because the dopamine response to multiple CSWs decays due to the adsorption properties of dopamine to CFM. However, there were still some non-faradaic components present in the signal due to changes in capacitive charging currents among CSWs. To eliminate the non-faradaic signal, the cyclic square wave voltammograms (CSWV) were modelled using the data in FIG. 2A, mimicking a capacitive current difference pattern to minimize the background current difference (FIG. 2B). Typically, voltammetry techniques that apply potential steps generate large capacitive charging currents that rapidly decrease while the potential is held constant (see FIG. 1C). In addition, the large capacitive current decays faster than the current due to the redox reactions. To exploit this feature, all current responses generated using M-CSWV were sampled (e.g., rather than sampling only at the end of each potential pulse after the capacitive current has decayed). Because all of the current was sampled, the capacitive charging contribution could be modelled and subtracted out.

It was hypothesized that the capacitive charging current response could be estimated with exponential decay modelling. The background current for each raw CSWV was thus modelled (FIG. 8A) using a one phase exponential decay equation ($Y=a \cdot e^{-bx}$, FIG. 8B). At each upward and downward staircase potential, five points from the peak current were discarded. Then, the next six points and last 20 points were used for modelling with the one phase exponential decay equation (FIG. 8B). By interpolating data in the middle of the decay curve, the slow redox reactions could be preserved while eliminating fast capacitive current decays. The modelled background current mimicked the difference pattern in FIG. 8A (FIG. 8B). Thus, by subtracting the modelled background current from raw signal, the capacitive current in the voltammogram could be minimized (FIGS. 2C and 8C). The dopamine redox response to M-CSWV was subsequently calculated by subtracting the resultant voltammograms from FIGS. 2A and B, (FIG. 2C).

Figures 2D, 2E:
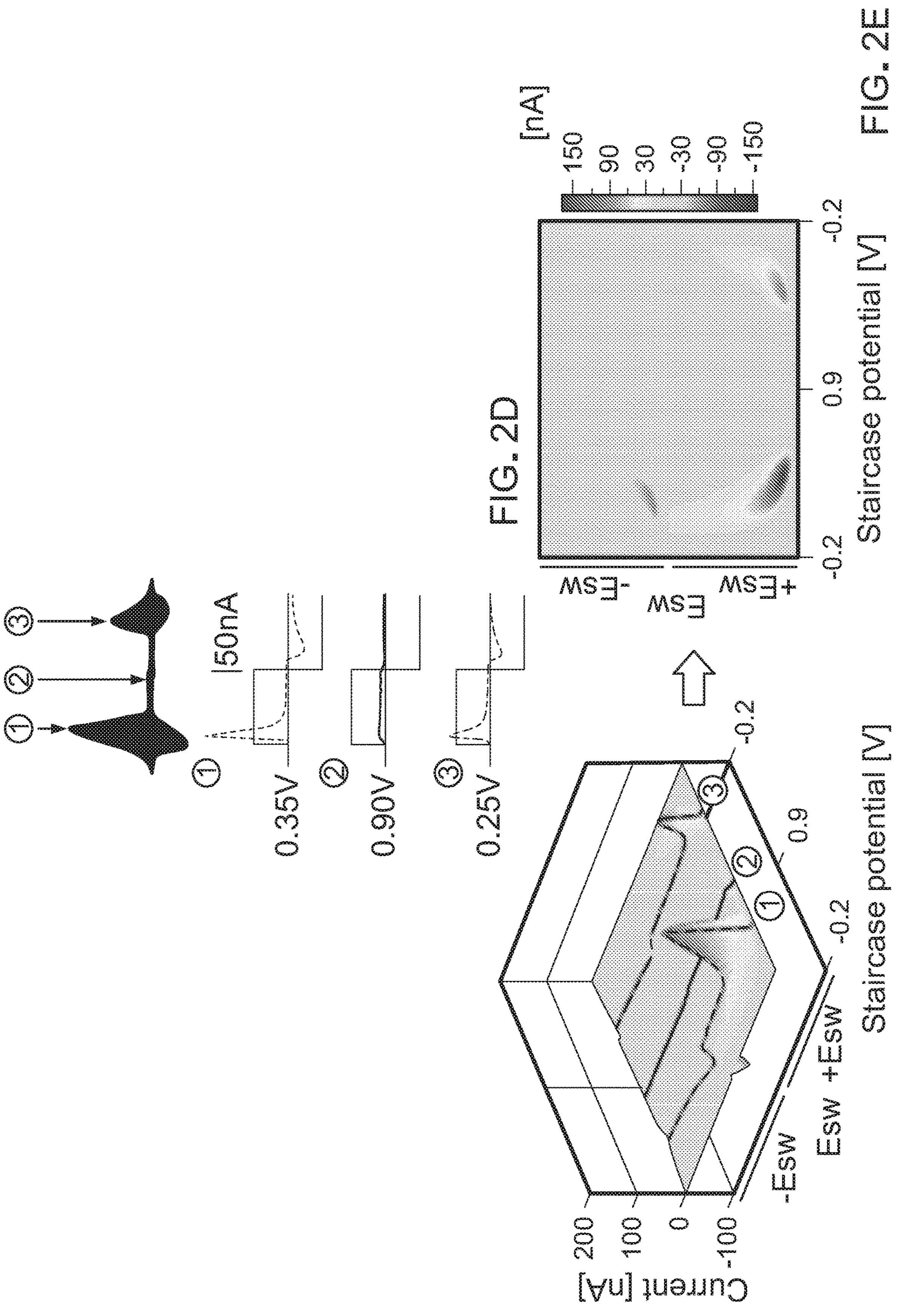

The dopamine response to M-CSWV consisted of redox reactions at both forward and reverse sweeps because the square wave modulation covers the redox potential range within a square wave. A maximum dopamine oxidation response occurred at a forward sweep staircase potential of 0.35 V (upward potential: 0.75V, downward potential: −0.15V, FIG. 2D-①). The dopamine redox reaction also occurred during the reverse sweep as well at 0.25 V (upward potential: 0.65V, downward potential: −0.25V, FIG. 2D-③). As shown in FIG. 2D-②), when the staircase potential did not cover the redox potential, there dopamine redox reactions were absent.

The dopamine responses were plotted (FIG. 2D) in an effort to provide a better visualization of the data. Plotting involved arranging the square wave responses in the order of the staircase potential (FIG. 2E). The x-axis is the staircase potential, ranging from −200 mV to 900 mV and back. The staircase potential was modulated with a square wave of ±400 mV, and this is plotted on the y-axis. The peak current of the redox response was the only information extracted from FIG. 2D. However, dissecting the response into a 2D array enabled a two-dimensional voltammogram (2D voltammogram) to be generated for each scan. The generation of this additional dimension provided significant new electrochemical information, such as a two dimensional signature of the redox reaction for each analyte. Thus, 2D voltammograms provide enhanced selectivity to dopamine, compared to conventional FSCV.

Optimization of M-CSWV Parameters to Dopamine Response $E_{holding}$, $E_{SW}$, and the number of waveforms applied were examined in an effort to optimize the dopamine response. When optimizing $E_{SW}$, the final peak potential ($E_{Peak}$+$E_{SW}$) was set at 1.3V to maximize sensitivity while not causing excessive charging current. The actual CSW that was used in this process is shown in FIG. 7. Using CSW from FIG. 1A, multiple CSWs were made with a 2.0 ms gap between each CSW, which is an optimal distance for negligible voltammetric cross talk among waveforms (FIG. 2B). M-CSWV was applied every 10 seconds to allow sufficient time for dopamine to reach equilibrium between the solution and the CFM surface dopamine concentration. Both upward/downward potentials generated upward/downward currents as shown in FIG. 1C.

Figure 3B:
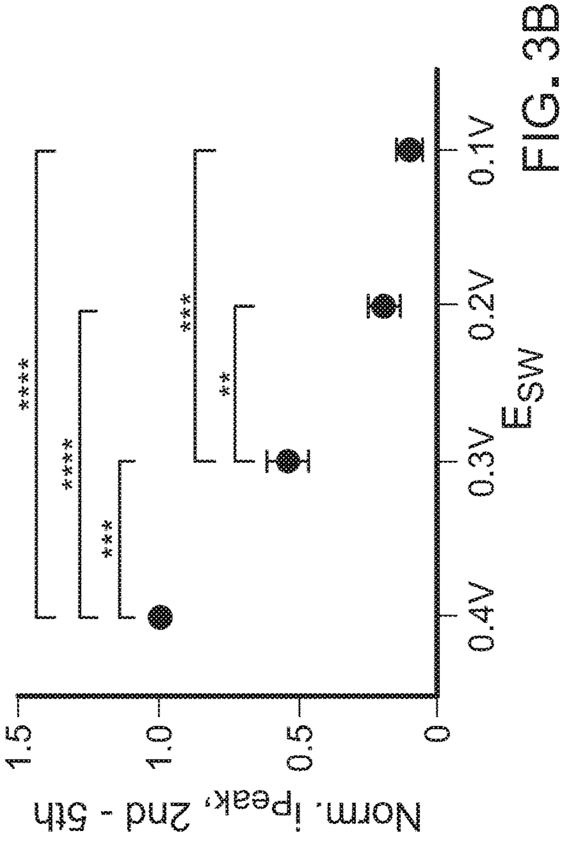
FIGS. 3A-3C depict parameters for optimal dopamine response of M-CSWV.
Figure 3A:
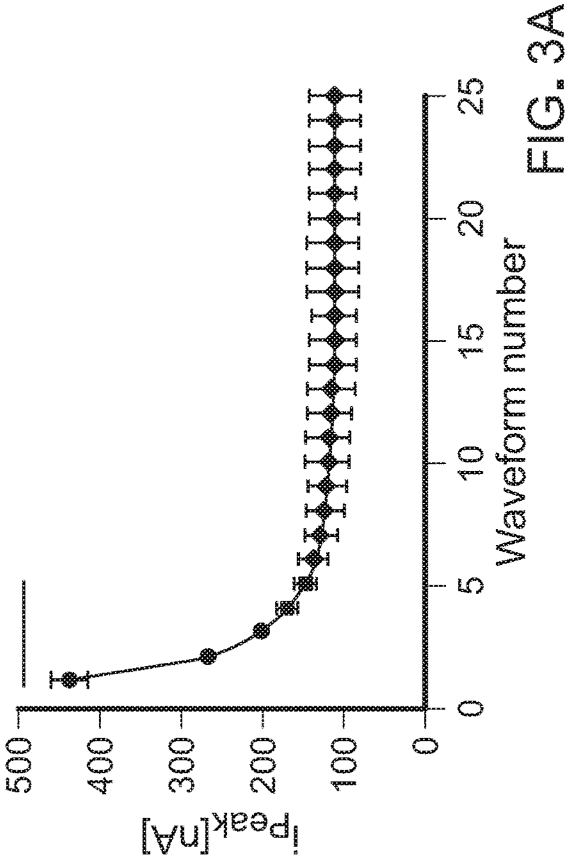

Among the multiple parameters that dictate the M-CSWV waveform, a possible avenue to improve sensitivity was investigated by measuring the dopamine sensitivity as a function of the number of waveforms applied, $E_{SW}$, and $E_{Holding}$ (FIG. 3). Previous voltammetric techniques utilized a wide range of repetition times (0.1 Hz to 100 Hz) to generate different dopamine responses within multiple waveforms. Since the dopamine response difference is directly related to the sensitivity, the number of CSWs used in M-CSWV must be determined. Therefore, M-CSWV composed of 25 CSWs was used to examine the dopamine response using the conventional background subtraction method (i.e. subtract the signal in buffer from the signal with dopamine present). Responses with 1 μM of dopamine decayed from 400 nA to 100 nA throughout 25 CSWs (FIG. 3A). In FIG. 9, the representative data showed that dopamine responses decayed until 5th or $6^{th}$ CSW. Statistically, the first through the fourth waveform showed significant differences when compared to the 25th dopamine signal (FIG. 3A, n=5 electrodes, p<0.0001, one-way ANOVA test with Dunnett's multiple comparisons, p<0.0001, DF=24, MS=24709, F=41.69). The 5th waveform to the 24th showed no significant difference; therefore, five CSWs were chosen as optimal to minimize the measurement time while maximizing sensitivity.

Next, $E_{SW}$, the amplitude of square wave, was examined and varied from ±100 mV to ±400 mV in 100 mV intervals. The number of waveforms was held constant at five. In the representative data shown in FIG. 10, the dopamine redox response increased as $E_{SW}$ was made larger. FIG. 4B shows the changes in the normalized M-CSWV response ($2^{nd}$-$5^{th}$) to 1.0 μM of dopamine as $E_{SW}$ was varied. An $E_{SW}$ of 400 mV was used for normalizing. The increases in M-CSWV response from $E_{SW}$ 100 mV to 400 mV can be explained by the larger potential range covered for both oxidation and reduction at each individual square wave. $E_{SW}$ 0.4V was chosen for M-CSWV because it showed significantly higher sensitivity than other potential steps (n=3 electrodes, p<0.0001, one-way ANOVA test with Tukey's multiple comparisons, DF=3, MS=0.4966, F=72.78). Potential steps beyond 400 mV were not included in FIG. 3B as they generated too large of a capacitive charging current, making quantification difficult.

Figure 3C:
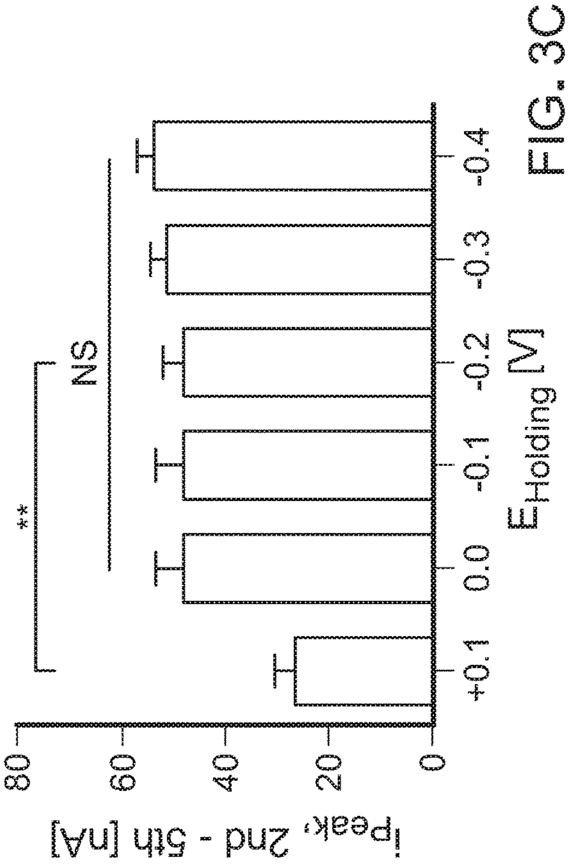

To further evaluate the effect of the applied waveform on dopamine sensitivity, the holding potential, $E_{Holding}$, was investigated. Dopamine is positively charged and it is known that the holding potential affects the adsorption of dopamine to CFM. Therefore, with the holding potential held at a positive potential (0.1V), the dopamine response was significantly lower than that with negative holding potentials (FIG. 3C, n=5 electrodes, one-way ANOVA test with Tukey's multiple comparisons, p<0.01, DF=5, MS=490.5, F=6.553). There was no significant difference in $i_{peak}$ values with the $E_{Holding}$<0.0 V as shown in FIGS. 3C and S-5. Therefore, a $E_{Holding}$ potential of 0.0 V was chosen because a lower capacitive charging current has been shown with a 0.0 V holding potential.

Dopamine-Kernel to Analyze M-CSWV

Figure 4A:
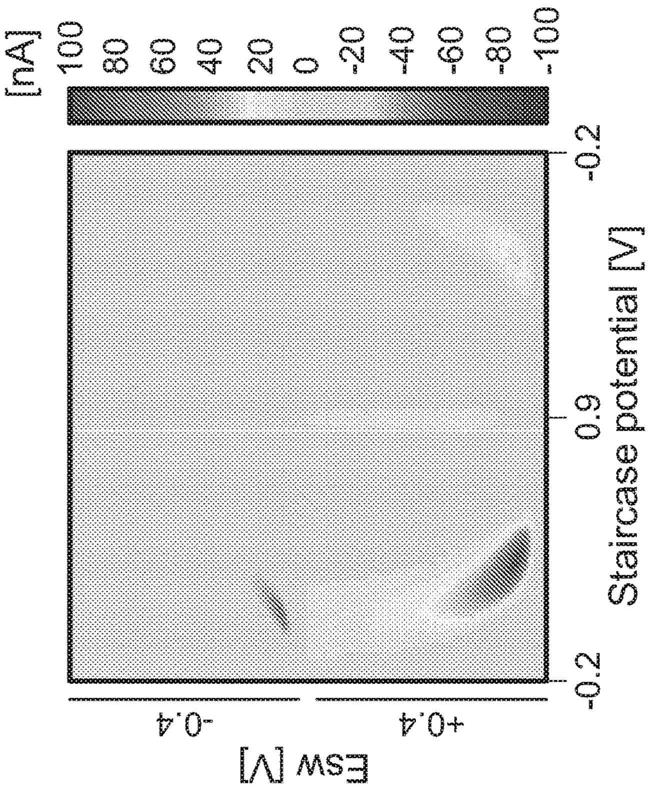
FIGS. 4A-4D illustrate Dopamine response to M-CSWV and analysis for calibration.
Figure 4B:
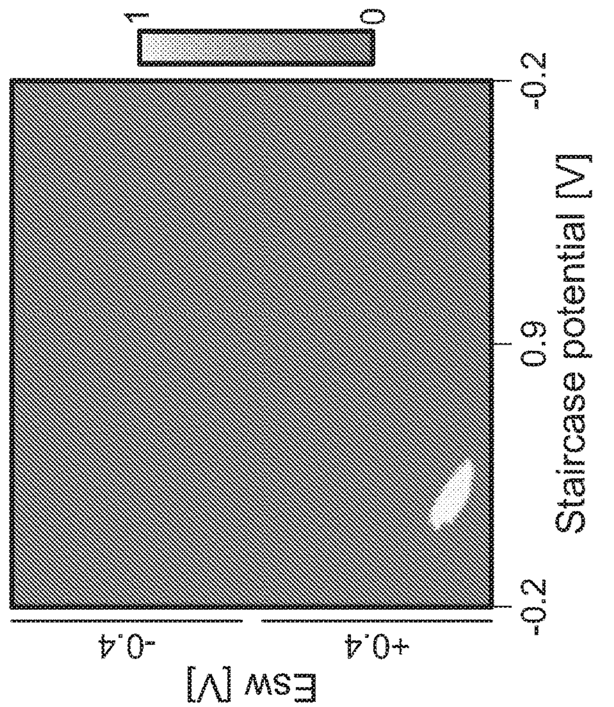
Figure 4C:
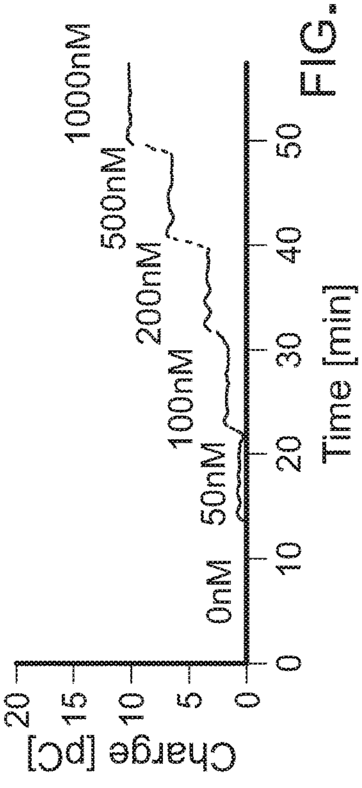
Figure 4D:
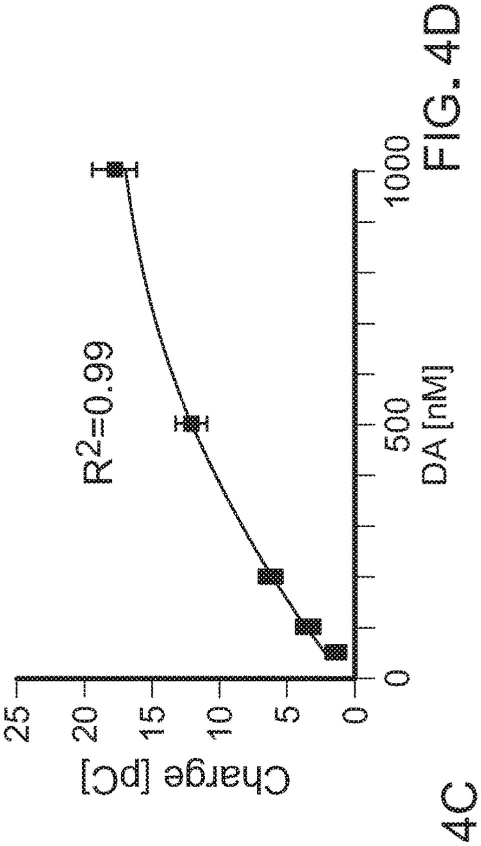

To develop a method for dopamine quantification, the above optimized parameters were used to collect 2D voltammograms in vitro using M-CSWV (FIG. 4A). In this regard, extracting relevant features from the 2D voltammogram can facilitate quantification of the concentration of dopamine. Here, a "dopamine-kernel" was developed and applied to the 2D voltammogram to extract the dopamine features. To make a dopamine-kernel, the in vitro dopamine response of M-CSWV was used and applied to a threshold algorithm where signals greater than 60% of the maximum current in the 2D voltammogram were given a value of one in the dopamine kernel to identify the oxidative features. The remaining points are given a value of zero (Yellow and red, respectively, in FIG. 4B). The dopamine-kernel was then extracted and applied to the 2D voltammogram by element-wise multiplication. This resulted in extracting only the dopamine-feature area from 2D voltammogram, which was then integrated. The integration of the dopamine-feature area corresponded to dopamine concentration (FIG. 4C, Video 0 Calibration) and the calibration curve followed a quadratic regression (n=4 electrodes, $R^2$=0.99). The accuracy of M-CSWV with the integration method resulted in higher sensitivity (31 pC/μM, with a limit of detection of 0.17±0.03 nM, ±SEM, n=4 electrodes) as previously reported. This may be attributed to the fact that the accumulated redox reaction is measured multiple times within a single scan. These results demonstrate that the produced dopamine-kernel improves the estimation of dopamine concentrations from the responses to M-CSWV. Principal component analysis may be also applied to facilitate measurement of dopamine or other analyte concentrations, including making use of the information-rich 2D voltammogram.

Selectivity for Dopamine Over Electroactive Interferents

Figure 5A:
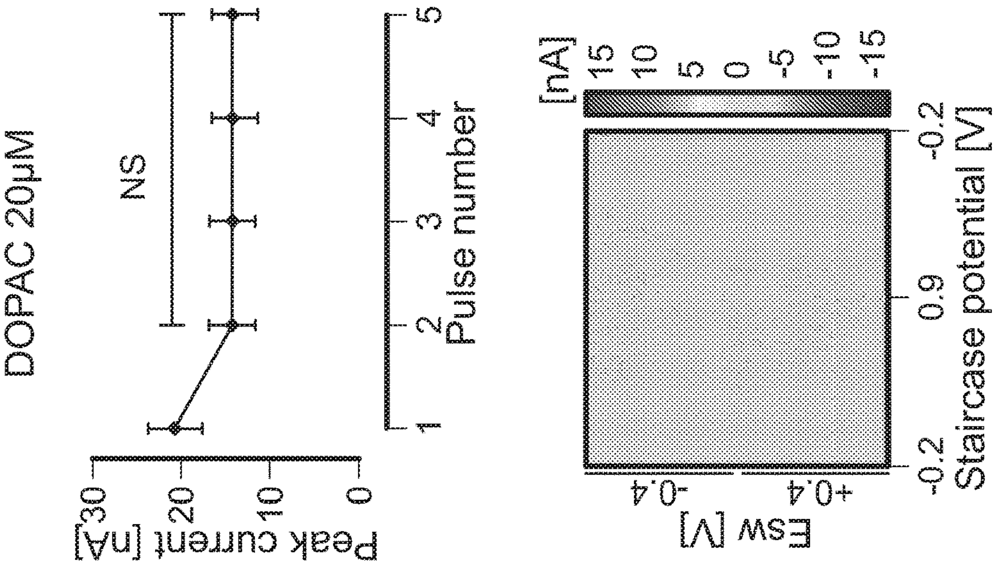
FIGS. 5A-5C illustrate M-CSWV responses for DOPAC, AA, and pH change.
Figure 6A:
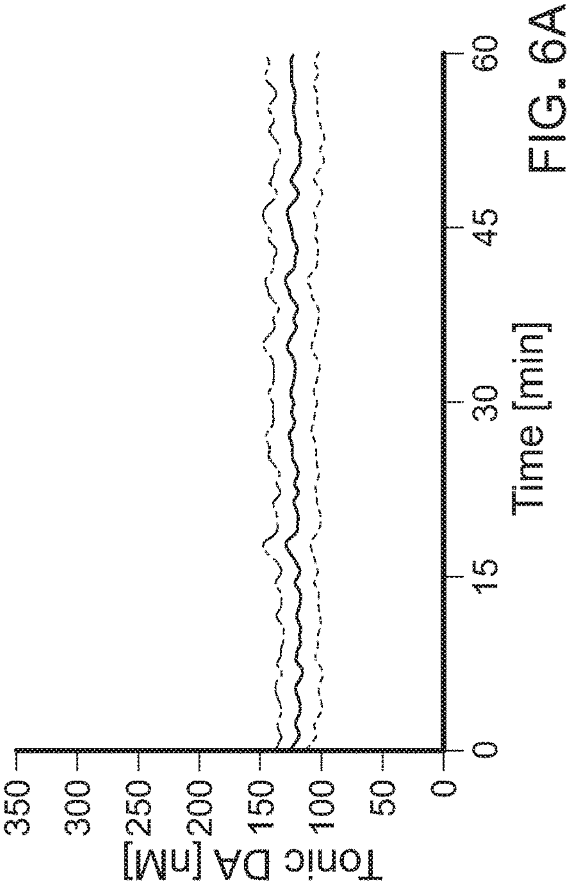

The method was tested against three common interferents in the rat striatum: two electroactive species, 3,4-dihydroxyphenylacetic acid (DOPAC, 20 μM) and ascorbic acid (AA, 200 μM), and a pH change (Δ −0.2). DOPAC is a primary metabolic byproduct of dopamine by monoamine oxidase and is thought to be present at 10 to 20 μM in the extracellular space. Ascorbic acid is a major antioxidant in the brain and its concentration is estimated to be in the range of 100 to 400 μM in the extracellular space. Both DOPAC and AA have similar redox potentials to dopamine and relatively much higher extracellular concentrations. The M-CSWV response to 20 μM DOPAC is depicted in FIG. 5A. Using conventional background subtraction, each CSWV response to DOPAC was able to be identified. As a result, the peak currents from 2nd to $5^{th}$ CSW were not significantly different (FIG. 5A, upper panel, n=5 electrodes, one-way ANOVA test, Tukey's multiple comparison, p=0.71, SS=120.0, DF=9, MS=13.33, F=0.69), which means that the dynamic background subtraction between $2^{nd}$ and $5^{th}$ can be used to offset DOPAC response to M-CSWV (FIG. 6A, lower panel). The representative background-subtracted DOPAC response showed that the $2^{nd}$ and $5^{th}$ 2 D voltammogram displayed identical redox patterns and the difference between $2^{nd}$ and $5^{th}$ response became zero (FIG. 12A).

Figure 5B:
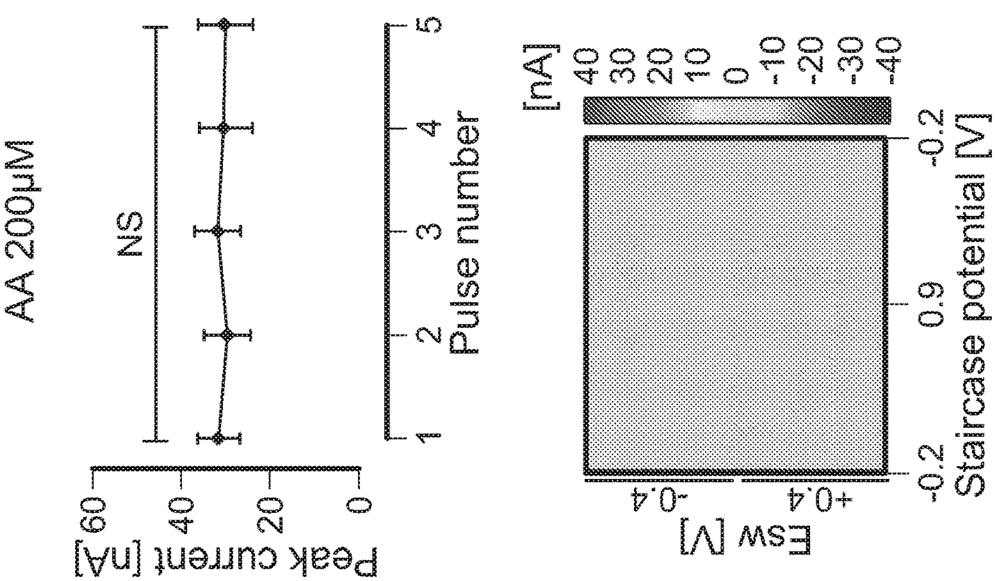
Figure 5C:
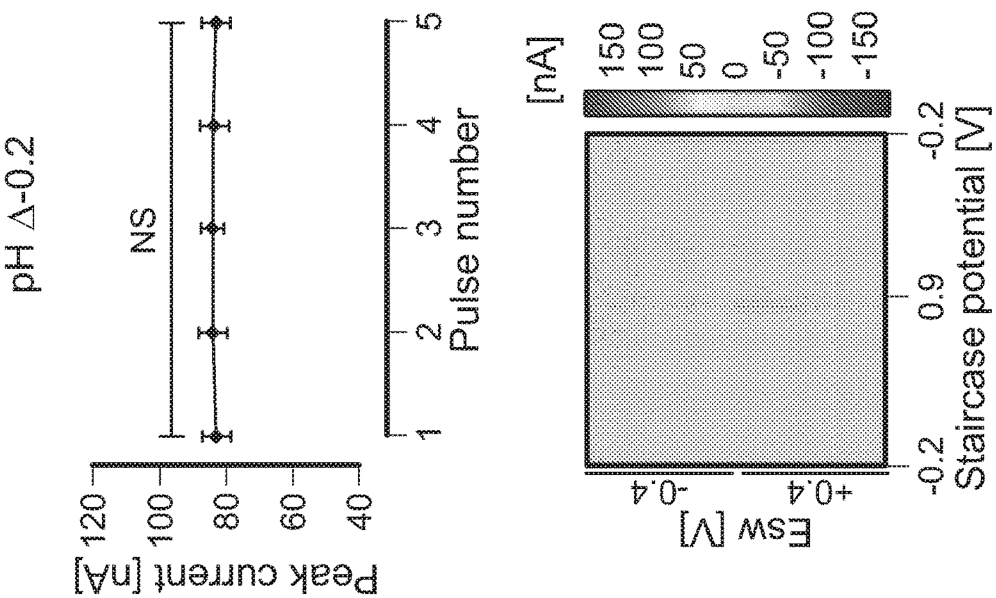

AA showed similar results with DOPAC, but AA expressed no significant peak currents differences from the 1st CSW (FIG. 5B, upper panel, n=5 electrodes, one-way ANOVA test, p>0.9999, SS=12.31, DF=9, MS=1.367, F=0.01423). The M-CSWV response to AA was also offset by subtracting $2^{nd}$ and $5^{th}$ (FIG. 5B, lower panel). The representative response of background-subtracted AA is shown in FIG. 12B. In FIG. 12B, AA responses in both $2^{nd}$ and $5^{th}$ CSW were also identical. These results are consistent with results previously reported. DOPAC and AA are known for low or non-adsorptive species at CFMs resulting in low sensitivity and fast equilibrium states in multiple pulses. Transient local pH changes in the brain is an accompanying phenomenon with neuronal activity and it has been a major contributor to capacitive background drift in voltammetry. The features of M-CSWV allow the removal of capacitive charging currents which includes the background drift caused by pH changes. The pH changes showed identical peak currents through all CSWs and the M-CSWV response was also offset (FIG. 5C, n=5 electrodes, one-way ANOVA test, p>0.9999, SS=4.269, DF=9, MS=0.4743, F=0.01042). A representative response of background-subtracted pH changes is shown in FIG. 12C. Other possible electroactive interferents (homovanillic acid, uric acid, and adenosine) were examined in vitro to confirm selective measurement of tonic dopamine levels in vivo. Homovanillic acid (HVA; 20 μM), uric acid (100 μM), and adenosine (1 μM) resulted in no significant difference in peak current from 1st CSW to 5th CSW, respectively (FIG. 13, n=3 electrodes, one-way ANOVA test). These results were expected as these analytes do not significantly adsorb to the carbon fiber surface, compared to dopamine. By adopting a dynamic background subtraction method, enabled confirmation that DOPAC, AA, pH changes, HVA, uric acid, and adenosine do not significantly impact the M-CSWV acquired dopamine response.

Effect of Increased Background Charging Currents on Local Neuronal Activity

Although the currents typically associated with electrochemical measurements performed at microelectrodes (Ø=7 μM, 50 μM in length) may not be sufficient to affect local neuronal activity, the charging current generated by M-CSWV is large (>10 μA, FIG. 1C) when compared to previous voltammetric techniques such as FSCV. To test if the currents generated by the application of M-CSWV would stimulate local neurons, a brain slice $Ca^{2+}$ imaging experiment was performed. A CFM was placed in a mouse striatum slice and the M-CSWV waveform was applied while the $Ca^{2+}$ recordings were made. Eight cells adjacent to the CFM surface were chosen from the microscopic field (FIG. 14A) and the increases in $[Ca^{2+}]$ were calculated and expressed as ΔF/F. The cells responded to KCL aqueous solution introduction and electrical stimulation (200 μA, biphasic, 2 ms pulse width, and 180 pulses). The conventional FSCV waveform (1.3V peak potential and 400 V/s) did not significantly affect the cell activity as previously reported. The M-CSWV waveform also did not significantly affect cell activity (FIG. 14B). Thus, it is highly unlikely that the M-CSWV generated currents do not affect or stimulate cells adjacent to the CFM despite its large capacitive charging current.

Determination of Tonic Dopamine Levels In Vivo by M-CSWV

To determine the average baseline "tonic" level of dopamine in vivo, M-CSWV was applied every ten seconds to the CFM implanted in the dorsomedial striatum of anesthetized rats for one hour (FIG. 6A). The average baseline dopamine levels were 120±18 nM (n=7 rats, ±SEM). Tonic extracellular dopamine concentrations measured in rat brain by microdialysis or electrochemical methods are listed in FIG. 15. Although these levels are ten-fold higher than those reported in previous microdialysis studies, our data is in accordance other studies that use modified voltammetric techniques to measure tonic dopamine concentrations in vivo. Microdialysis has been the gold-standard technique to detect tonic extracellular dopamine concentrations because it provides high selectivity given that samples are analysed ex situ with chemical separation techniques, such as high performance liquid chromatography and capillary electrophoresis. However, significant limitations imposed by the time required for molecules to equilibrate across the dialysis membrane, the time required to collect sufficient sample size for analysis (temporal resolution of 1 to 20 minutes), and most importantly, tissue damage caused by the length and diameter of the dialysis membrane prevent the ability to continuously monitor dopamine levels. In contrast, this study indicates that M-CSWV can offer superior time resolution (a measurement every 10 seconds) and spatial resolution (7 μm diameter and 50 μm in length) for in situ detection of dopamine. These features provide a much lower equilibrium time between the carbon fiber and dopamine molecules for a higher sampling rate.

Figure 6B:
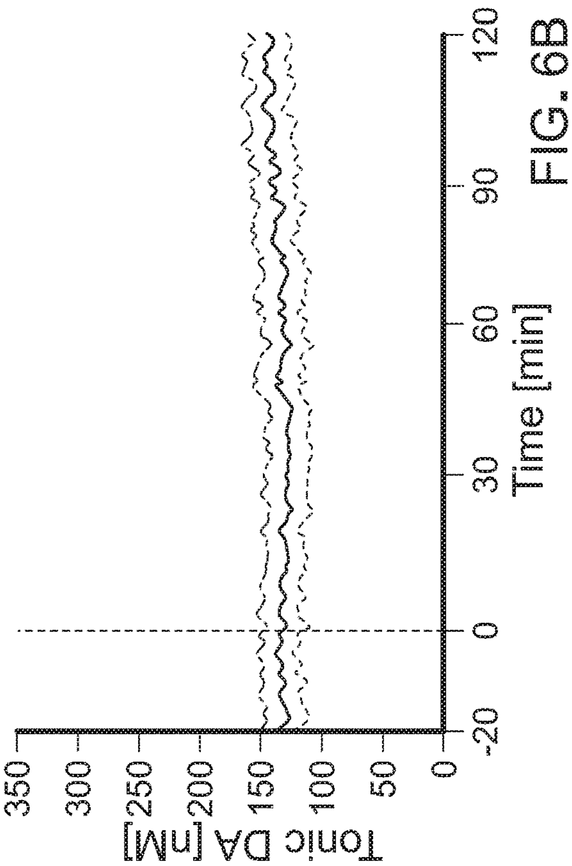
Figure 6C:
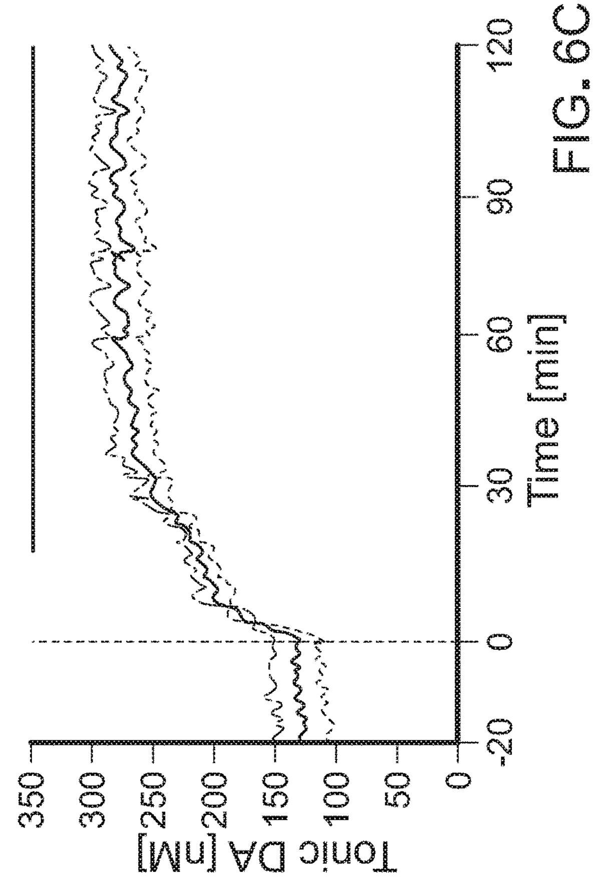

Pharmacological treatments with different dopaminergic agents designed to modulate tonic dopamine levels were also conducted to confirm M-CSWV selectivity for in vivo dopamine detection. I.p. injection of saline did not alter dopamine tonic levels recorded for 2 hours following injection (FIG. 6B, 135±15 nM, n=5 rats, Video 1_Saline). After dopamine is released, it is rapidly cleared from the extracellular space by the dopamine transporter DAT expressed in the pre-synaptic terminals, soma, and dendrites of dopaminergic neurons. Pharmacological inhibition of DAT with nomifensine or cocaine has been used to show enhanced tonic and phasic levels of dopamine in an activity-dependent manner. Systemic administration of the DAT blocker, nomifensine, caused an increase in tonic levels of dopamine that reached a plateau twofold higher than pre-drug baseline levels after 40 min (FIG. 6C, n=5 rats, Video 2_Nomifensine). The average tonic dopamine level elevated from 130 nM to 279 nM after the injection of nomifensine and reached significance ~23 minutes after the injection (FIG. 6C, upper bar, n=5 rats, two-way ANOVA, p<0.0001, DF=4, MS=22863, F=17.88).

There is a possibility that the tonic measurements obtained in this study were partially impacted by increased norepinephrine (NE) levels because nomifensine exhibits equal affinity for DAT and the NE transporter (NET). In addition, dopamine can be cleared from the extracellular space by NET in brain regions where dopaminergic projections are relatively low, such as the prefrontal cortex and hippocampus. However, NE tissue content in the striatum is negligible and it has been demonstrated that the local infusion of selective NET inhibitors do not affect dopamine levels in the striatum.

Figure 6D:
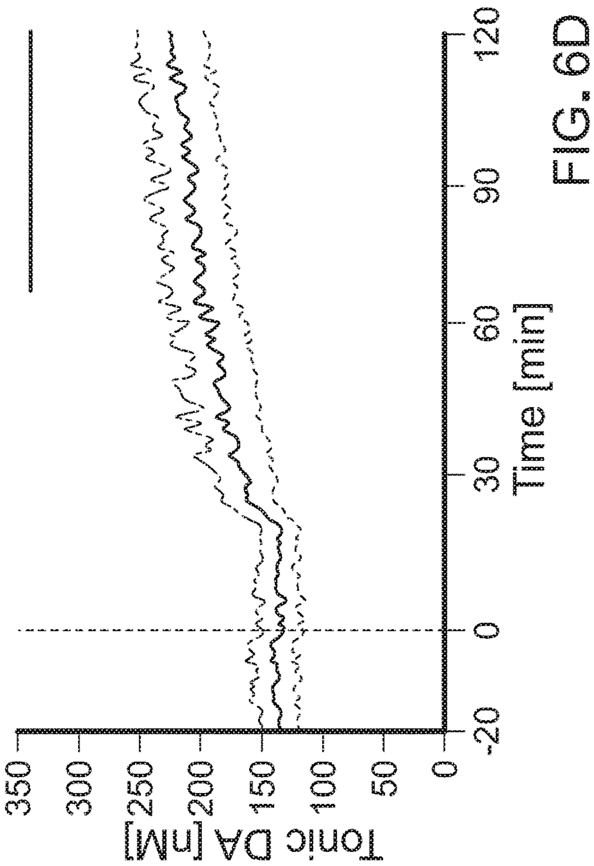

As well, it was determined that the signal was also not due to the electroactive dopamine metabolite DOPAC. After dopamine reuptake, the neurotransmitter is metabolized to DOPAC primarily by MAO, a mitochondrial enzyme that oxides the side chain of dopamine. As shown above (FIG. 5A), M-CSWV was able to cancel out DOPAC by dynamic subtraction. To examine whether the signal originated from DOPAC in vivo, the MAO inhibitor pargyline was administered. Inhibition of MAO by pargyline resulted in a delayed and relatively slow increase in striatum tonic levels of dopamine (FIG. 6D, video 3_Pargyline). The rate of dopamine metabolism by MAO is sufficiently slow that it plays little role on the time scale of phasic bursting activity. Hence, no immediate changes have been observed in FSCV recordings of stimulation-evoked dopamine release following MAO inhibition. However, MAO inhibition significantly increases tonic dopamine, because its intraneuronal metabolism competes with its repackaging into vesicles, increasing the availability of dopamine for activity-dependent release. Injection of pargyline elevated the tonic dopamine level from 135 nM to 225 nM for two hours. Because of the slow metabolism, the effects of pargyline on tonic dopamine levels reached significance ~68 minutes after injection (FIG. 6D, upper bar, n=5 rats, two-way ANOVA, p<0.0001, DF=4, MS=244587, F=358.5).

FIG. 16 depicts a flowchart of an example process 1600 for determining a level of an analyte in a solution using M-CSWV. At stage 1602, an electrode (e.g., a carbon fiber microelectrode) is located in a solution having an analyte present therein. For example, the electrode may be placed in neural tissue having a solution with dopamine and other neurochemicals therein. At stage 1604, the electrode applies an electrical stimulus to the solution based on a multiple cyclic square waveform (M-CSW). The electrode or another electrode is used to measure an electrical current response to the stimulus (stage 1606), and a level of analyte in the solution is determined based on the electrical current response (stage 1608).

Example Implementation #2: Sloped-Edge Waveforms

As has been described, to perform M-CSWV, a characteristic voltage waveform is applied to neural tissue via an electrode, e.g., a carbon-fiber microelectrode. A voltammetric system coupled to or including the electrode produces the waveform and records the resulting current as a function of the applied voltage. For M-CSWV, the waveform can be based on a square wave that is incremented in voltage, period by period, until a defined peak voltage is reached, and then is decremented in voltage, period by period, back to the baseline voltage.

Application of a changing voltage to a neural electrode can produce a "background" current that is roughly proportional to the rate of change (ΔV/Δt) of the signal. The double layer of charge at the electrode-electrolyte interface acts like a capacitor. The level of background current can also be a function of the surface area of the electrode. For traditional voltammetry in neuroscience applications, the scan rates (ΔV/Δt) of applied waveforms rarely exceed 1,000 V/s, resulting in background currents of just a few microamperes (e.g., ±3 μA). For M-CSWV, however, much higher scan rates can be employed (e.g., scan rates of up to 80 kV/s have been achieved). These high scan rates can produce much larger background currents (e.g., ±20 μA)—sometimes large enough to stimulate action potentials and even damage neural tissue. To prevent stimulation and tissue damage, smaller microelectrodes have been employed but at the expense of a reduction in sensitivity.

In some implementations, a waveform generator for M-CSWV uses a digital-to-analog converter (DAC) integrated circuit (IC) to very rapidly jump between low and high voltages. For example, the DAC IC may jump from one voltage to the next to produce a square wave with just a 10-μs long rising or falling edge for a 0.8 V step. It should be understood that the rise/fall time for a single step of a DAC from one output voltage to another may not be inherently controllable, but rather may be dependent on factors such as the load impedance, particularly capacitance, and the slew-rate capabilities of the DAC's output amplifier (which may or not be intrinsic to the DAC IC). In one working example, rising/falling edges of about 10 μs were produced. In view of the difficulties with controlling the slope of rising or falling edges produced by the DAC, in some cases it is preferable to use additional circuitry to adjust and control the slopes of the rising and falling edges of the square wave. For these implementations, the circuitry employed for the relatively simple square-wave generator may be insufficient to permit such variability and control. Nonetheless, varying the waveform slope can be beneficial in that it permits the scan rate in M-CSWV to be reduced (e.g., by 25-percent or more) while achieving comparable results to higher scan rates without adjustable or controllable edge rise/fall times. The lower scan rate in turn reduces the background current that results from the change in applied voltage. With lower scan rates and reduced background currents, larger microelectrodes can be employed in vivo on the neural tissue without risking stimulation or tissue damage while increasing the sensitivity levels that can be achieved.

The waveform generator for the adjustable-sloped multiple cyclic square wave can also increase linearity of the edges while transitioning from a low to high voltage, or vice versa. In contrast to other approaches where each edge may resemble a gentle S-curve comprising a range of slopes, for example, the improved edge linearity of the disclosed generator can reduce noise in instantaneous deviations of the background current.

In some implementations, the waveform generator can produce waveforms for M-SCWV with ramps/edges of controllable slope through use of a DAC-controlled current source to charge and discharge an integrating capacitor. The integrating capacitor's rate of change of voltage (±ΔV/Δt) can be directly proportional to the current source's input voltage. The capacitor voltage, buffered and applied to the electrode (e.g., carbon fiber microelectrode), produces a linear rising or falling edge. In some examples, only one DAC setting is required to produce a controlled rising or falling edge, thereby reducing occurrences of DAC glitching and digital-feedthrough. Moreover, complex waveforms that incorporate both sloped and constant intervals can be produced by summing a ramp generator output with the output of a separate DAC. And although the waveform generator presents specific benefits for M-CSWV, it can also be applied to generate appropriate waveforms for traditional fast-scan cyclic voltammetry.

Adjustable-Slope M-CSWV Waveforms: Circuitry and Method

The circuitry for a waveform generator that produces a square wave with adjustable slope can include a modified current pump. FIG. 17 is a schematic for Howland Integrator circuit 1700 that can be employed in the waveform generator for this purpose. The Howland Integrator 1700 includes a Howland current pump with an integrating capacitor 1704 hanging off the noninverting input terminal of the operational amplifier (op-amp) 1702. If the resistances of resistors R1-R4 are equal, then the following expressions define the integrating function of the Howland Integrator 1700:

$$Vramp(t) = \frac{2}{RC}\int Vin1(t)dt \text{ Where } Vramp(t=0) = 0\ V,$$

with reset switch open.

$$Vramp(t1) = \Delta V = \frac{2}{RC} Vin1\Delta t \text{ At } t = t1, \text{ if } Vin1 \text{ is a constant.}$$

$$\therefore \frac{\Delta V}{\Delta t} = SR = \frac{2\ Vin1}{RC} \text{ Where } SR = \text{scan rate (slope).}$$

Thus, with the Howland Integrator a rising or falling $V_{ramp}$ of arbitrary slope can be produced by applying a constant input voltage $V_{in1}$. For a positive (rising) slope, the input voltage is positive; for a negative (falling) slope, the input voltage is negative. If $V_{in1}$=0 V, then $V_{ramp}$ remains constant.

The above derivation assumes the capacitor's reset switch 1706 is set to the open position. However, the switch 1706 can be a three-way switch that can be set in either a first position (open) so that the circuit 1700 behaves as described above, a second position that clamps the capacitor 1704 (C1) to $V_{in2}$, or a third position that connects the capacitor to 1704 (C1) to ground. Because capacitor 1704 (C1) and the series resistance in the reset switch circuitry are both small, the capacitor can be discharged to ground (0 V) quickly. However, clamping to $V_{in2}$ would be practical only if the $V_{in2}$ source was sufficiently stiff (e.g., a battery or a very large capacitor). A voltage source with a control loop, e.g., a buffered DAC or an amplifier (including "unlimited capacitive load" op-amps), would generally be incapable of driving C1 to a settled voltage quickly enough, and to do so without overshoot and excessive ringing.

In the preceding example, when V(C1) is clamped to $V_{in2}$, $V_{ramp}=2(V_{in2})+2(V_{in1})(Rx/R)$, where R is the value of the four Howland Integrator resistors R1-R4 and Rx is the series resistance of the clamp switch. In this case, Rx (~3 Ohms) is much smaller than R, and as such $V_{ramp}$ approximately equals $2(V_{in2})$.

FIG. 18 depicts a segmented FSCV waveform produced by the Howland Integrator circuit 1700. The waveforms applied as inputs $V_{in2}$ and $V_{in3}$ are shown along with a time plot of clamping applied to capacitor 1704 (C1) via switch 1706, and the resulting output voltage $V_{out}$. The figure spans ~30 ms in this example. Specifically, in this instance, capacitor 1704 (C1) is clamped to ground (0 V) during all constant-voltage intervals of $V_{out}$. In this way, $V_{out}=V_{in3}/2$ during the constant-voltage segments. C1 is then unclamped when a rising or falling voltage is to be produced. FIG. 19 depicts a segmented FSCV waveform, produced with C1 unclamped during the short (~2 ms) constant-voltage intervals, as well as during all sloped segments.

Complex waveforms with nonzero constant-voltage segments, such as those illustrated in FIGS. 18 and 19, can be produced by applying a DC voltage ($V_{in3}$ in FIG. 17) to the summing circuit, which in the circuit 1700 is formed by tying two resistors together. During a constant-voltage segment, C1 is clamped to ground (as in FIG. 18), but if the constant-voltage segment is brief (e.g., 1-2 ms), then C1 can be left unclamped, with $V_{in1}$ set to ~0 V, such that $V_{ramp}$ remains constant (see FIG. 19). Note that calibration may be necessary to determine the precise voltage level for $V_{in1}$ that produces a constant $V_{ramp}$. Calibrated DAC settings can compensate for variability of the Howland Integrator RC values, op-amp offsets, and DAC error, for example.

The endpoint voltage for any sloped segment of a waveform depends on the starting voltage, slope (as dictated by the level $V_{in1}$), and switch timing. For example, to produce a 400-V/s FSCV pyramid with a peak voltage of 1.4 V, $V_{in1}$ should be set to the appropriate (positive) voltage, the clamp switch 1706 should be set to the off position, hold these settings for a defined length of time (e.g., 3.5 ms), then $V_{in1}$ from the positive voltage to an appropriate negative voltage, hold these settings for a defined length of time (e.g., 3.5 ms), and then turn the clamp switch back on to clamp the capacitor to $V_{in2}$ (with $V_{in2}$ already set to the desired rest voltage).

A much faster waveform, illustrated in FIG. 20, is the square wave component of an M-CSWV waveform. Its rising and falling edges are only 10 μs long in the depicted example. Because $V_{in1}$ DAC's skew rate and settling time characteristics can be significant at this time scale, $V_{in1}$ can be set prior to removing the clamp at the start of the rising edge. The clamp can be left off during the 0.5-ms "top" of the square wave. However, the clamp is applied after the trailing edge of the square wave; if it were not clamped frequently, small voltage errors could accumulate over successive periods of the square wave, potentially resulting in unacceptably large error in the output voltage.

To produce an M-CSWV "chevron" waveform, $V_{out}$ is incremented by a set ΔV for each of N successive square wave periods, after which $V_{out}$ is decremented by ΔV for the same number of square wave periods. The incrementing and decrementing is accomplished by summing a square wave (as in FIG. 20) with a staircase waveform produced by $V_{in3}$, as illustrated in FIG. 21. For example, FIG. 21 illustrates that during the ascending half of the M-CSWV "chevron" waveform, $V_{in3}$ is incremented by 50 mV each square wave period and summed with the $V_{ramp}$ square wave. The resulting increment in the chevron waveform is 25 mV in this example. The $V_{in3}$ staircase decreases during the descending half of the M-CSWV waveform.

Adjustable-Slope M-CSWV Waveforms Example Implementation

To achieve high scan rates for M-CSWV (e.g., 80 kV/s), the Howland Integrator resistors and integrating capacitor can be much smaller than those used for slower scan rates applied in FSCV (e.g., 400 V/s). To provide a capability for use in both M-CSWV and FSCV contexts, a voltammetric system can include a pair of Howland Integrator ramp generators. A first ramp generator is configured for slow ramps (e.g., 400 V/s) while the second generator is configured for faster action, e.g., an 80-kV/s M-CSWV waveform. The slower ramp generator can employ larger resistors (e.g., 10 kOhms) and larger integrating capacitance (e.g., 0.2 μf). The faster ramp generator can employ smaller resistors (e.g., 5 kOhms) and a much smaller integrating capacitance (e.g., 0.008 μf). In some implementations, the system includes multiple analog switches (e.g., U12, U14, U15 and their sub-parts) that can be toggled to select one ramp generator or the other depending on the operation to be performed, e.g., FSCV or M-CSWV.

FIG. 22 depicts a schematic diagram of a waveform generation circuit 2200 for a voltammetric system. The circuit depicted in this figure includes two Howland Integrator sub-circuits: a first sub-circuit 2202 for slow ramp generation and a second sub-circuit 2204 for faster ramp generation (e.g., for FSCV and M-CSWV, respectively). An LPC1769 microcontroller (not shown) operates the two DACs 2206, 2208. One of the DACs (2206) produces the "$V_{in1}$" control input to the selected ramp generator. This input, i.e., $V_{in1}$, determines the slope of a rising or falling edge of the generated waveform (see FIGS. 18-20). The other DAC (2208) produces the "$V_{in3}$" DC offset that is added to the ramp generator op-amp voltage, as illustrated in FIG. 21. Concurrently, and in precisely defined sequence with the other two inputs, the microcontroller operates analog switch U17A (2210) or U17B (2212), clamping or releasing the integrating capacitors, in the manner illustrated in FIGS. 18-20. For example, the microcontroller may be configured to generate (i) a first signal $S_1$ provided to DAC 2206 to control and adjust the value of $V_{in1}$ (and thus the slop of $V_{ramp}$ and the resulting slope of the edges in the output waveform), (ii) a second signal Sd2 to DAC2208 to control and adjust the value of $V_{in3}$, and (iii) a third signal $S_3$ to DAC2208. In some implementations, the waveform generation circuit 2200 can be constructed on a single layer or multi-layered printed circuit board. Control inputs may be provided, for example, by a field programmable gate array (FPGA), a microcontroller, or both. In some implementations, an FPGA may be arranged to provide the control inputs for M-CSWV while a microcontroller is arranged to provide the control inputs for FSCV.

FIG. 23 depicts a flowchart of an example process 2300 for determining a level of an analyte in a solution using a multi-mode voltammetric system (e.g., a system including an electrode and multi-mode waveform generator). In some implementations, the process 2300 is carried out using the waveform generation circuit 2200 depicted in FIG. 22. At stage 2302, power is applied to a multi-mode (e.g., dualmode) waveform generator. At stage 2304, an operational mode is selected, e.g., according to a default setting or in response to user input. The waveform generator may be configured to operate in multiple modes according to the voltammetric function desired. For example, a first mode for fast-scan cyclic voltammetry (FSCV) may be selected, or a second mode for M-CSWV may be selected. In some implementations, within each mode, a user may specify operational parameters for the mode such as a scanning frequency and/or a slope of the rising and falling edges. At stage 2306, the waveform generator is configured to employ a specific sub-circuit corresponding to the selected mode, e.g., a slow ramp sub-circuit 2202 or a fast ramp sub-circuit 2204. The waveform generator is also configured to operate according to the selected mode and specified parameters within the selected mode. At stage 2308, the waveform generator generates an electrical waveform according to the selected mode and specified parameters, e.g., a multiple cyclic square waveform. At stage 2310, the waveform is delivered to a solution containing an analyte such as to a neural tissue sample. At stage 2312, a current response is measured based on the delivered electrical stimulus from the waveform. The current response can then be analyzed according to methods described herein or other methods as known (e.g., methods applied in FSCV) to determine levels of one or more analytes in the solution.

FIG. 24 depicts a flowchart of an example process 2400 for generating a sloped-edge square waveform. In some implementations, the waveform can be generated using the circuits depicted in FIGS. 17 and/or 22. The waveform is periodic, but the actions depicted in FIG. 24 represent generation of just a single period of the waveform. These actions can be repeated on a periodic basis to generate a continuous waveform. A single period of such a waveform is depicted, for example, in FIG. 20 by $V_{ramp}$.

At stage 2402, a rising edge 2002 of the waveform is produced with the waveform generator by (i) applying a first DC voltage as a first input to an integrator circuit for a first time interval and (ii) maintaining a capacitor in a de-clamped position for the first time interval.

At stage 2404, a high segment 2004 of the waveform is produced with the waveform generator to follow the rising edge by (i) switching the first input to the integrator circuit from the first DC voltage to a baseline DC voltage for a second time interval following the first time interval and (ii) maintaining the capacitor in the de-clamped position for the second time interval, wherein the high segment of the waveform maintains a high DC voltage for the second time interval, wherein the baseline DC voltage is less than the first DC voltage.

At stage 2406, a falling edge 2006 of the waveform to follow the high segment of the waveform is produced with the waveform generator by (i) switching the first input to the integrator circuit from the baseline DC voltage to a second DC voltage for a third time interval following the second time interval and (ii) maintaining the capacitor in the de-clamped position for the third time interval, wherein the second DC voltage is less than the first DC voltage and is less than the baseline DC voltage.

At stage 2408, a low segment 2008 of the waveform to follow the falling edge of the waveform is produced with the waveform generator by (i) switching the first input to the integrator circuit from the second DC voltage to the baseline DC voltage for a fourth time interval and (ii) setting the capacitor in a clamped position for the fourth time interval.

Computer-Based Implementations

In some implementations, analyte measurements using the M-CSWV techniques disclosed herein can involve computer-based systems, devices, and/or processes, such as to control parameters of the stimulation, to record data, to generate voltammogram plots, and/or to otherwise analyze data collected according to the disclosed techniques.

For such implementations, the computer-based aspects of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non transitory program carrier for execution by, or to control the operation of, data processing apparatus. Alternatively or in addition, the program instructions can be encoded on an artificially generated propagated signal, e.g., a machine-generated electrical, optical, or electromagnetic signal, that is generated to encode information for transmission to suitable receiver apparatus for execution by a data processing apparatus. The computer storage medium can be a machine-readable storage device, a machine-readable storage substrate, a random or serial access memory device, or a combination of one or more of them. The computer storage medium is not, however, a propagated signal.

The term "data processing apparatus" encompasses all kinds of apparatus, devices, and machines for processing data, including by way of example a programmable processor, a computer, or multiple processors or computers. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, or a combination of one or more of them.

A computer program (which may also be referred to or described as a program, software, a software application, a module, a software module, a script, or code) can be written in any form of programming language, including compiled or interpreted languages, or declarative or procedural languages, and it can be deployed in any form, including as a stand alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a communication network.

As used in this specification, an "engine," or "software engine," refers to a software implemented input/output system that provides an output that is different from the input. An engine can be an encoded block of functionality, such as a library, a platform, a software development kit ("SDK"), or an object. Each engine can be implemented on any appropriate type of computing device, e.g., servers, mobile phones, tablet computers, notebook computers, music players, e-book readers, laptop or desktop computers, PDAs, smart phones, or other stationary or portable devices, that includes one or more processors and computer readable media. Additionally, two or more of the engines may be implemented on the same computing device, or on different computing devices.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Computers suitable for the execution of a computer program include, by way of example, can be based on general or special purpose microprocessors or both, or any other kind of central processing unit. Generally, a central processing unit will receive instructions and data from a read only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A method for measuring a tonic level of a neurochemical in a neural tissue, comprising:

stimulating the neural tissue with an electrical stimulus produced by a waveform generator, the electrical stimulus comprising a multiple cyclic square waveform (M-CSW);

detecting, by an electrode in contact with the neural tissue while the neural tissue is stimulated with the electrical stimulus comprising the M-CSW, an electrical current response to the electrical stimulus, the electrical current response indicative of the tonic level of the neurochemical in the neural tissue; and adjusting, by the waveform generator, the electrical stimulus applied to the neural tissue based on the tonic level of the neurochemical indicated by the electrical current response.

2. The method of claim 1, wherein the neurochemical is dopamine.

3. The method of claim 1, wherein the neural tissue comprises a solution in a brain of a mammal.

4. The method of claim 1, wherein the electrode is a carbon fiber microelectrode.

5. The method of claim 1, wherein the M-CSW signal comprises a square wave oscillation superimposed on a staircase waveform, wherein the staircase waveform has a rising phase and a falling phase.

6. The method of claim 1, wherein the M-CSW includes sloped rising and falling edges.

7. The method of claim 1, further comprising adjusting a slope of rising or falling edges of the M-CSW by adjusting a DC input voltage to a waveform generation circuit.

8. The method of claim 1, further comprising generating a two-dimensional (2D) voltammogram from the measured electrical current response and using the 2D voltammogram to determine the tonic level of the neurochemical in the neural tissue.

* * * * *